US008189737B2

(12) United States Patent
Keller et al.

(10) Patent No.: US 8,189,737 B2
(45) Date of Patent: May 29, 2012

(54) PROCESS AND APPARATUS FOR MICROCT IMAGING OF EX VIVO SPECIMENS

(75) Inventors: Charles Keller, San Antonio, TX (US); Ali N. Bahadur, San Antonio, TX (US)

(73) Assignee: The Board of Regents, The University of Texas System, a Texas Institution of Higher Learning, San Antonio, TX (US)

( * ) Notice: Subject to any disclaimer, the term of this patent is extended or adjusted under 35 U.S.C. 154(b) by 500 days.

(21) Appl. No.: 12/162,376

(22) PCT Filed: Jan. 26, 2007

(86) PCT No.: PCT/US2007/002264
§ 371 (c)(1),
(2), (4) Date: Oct. 15, 2008

(87) PCT Pub. No.: WO2007/089641
PCT Pub. Date: Aug. 9, 2007

(65) Prior Publication Data
US 2009/0080600 A1   Mar. 26, 2009

Related U.S. Application Data

(60) Provisional application No. 60/762,327, filed on Jan. 26, 2006.

(51) Int. Cl.
*G01N 23/00* (2006.01)
*G06K 9/00* (2006.01)
(52) U.S. Cl. .......................................... 378/18; 382/131
(58) Field of Classification Search .................. None
See application file for complete search history.

(56) References Cited

U.S. PATENT DOCUMENTS

| 3,645,090 A | 2/1972 | Mochizuki et al. ................ 58/58 |
| 3,940,475 A | 2/1976 | Gross .................................... 424/1 |
| 7,067,269 B2 | 6/2006 | Dress et al. ................... 435/7.93 |
| 7,101,709 B2 | 9/2006 | Weiss et al. ..................... 435/377 |
| 7,230,242 B2 | 6/2007 | Behar et al. .................... 250/310 |
| 7,536,041 B2 | 5/2009 | Pekar et al. ..................... 382/131 |
| 2004/0223909 A1 | 11/2004 | Montalto et al. ............... 424/9.1 |
| 2005/0002552 A1 | 1/2005 | Dunn et al. ........................ 435/6 |
| 2005/0085543 A1 | 4/2005 | Walliman et al. ............. 514/310 |
| 2007/0236496 A1 | 10/2007 | Keller, III et al. ............ 345/619 |

FOREIGN PATENT DOCUMENTS

WO   WO 2004/048970   6/2004
WO   WO 2007/089641   8/2007

OTHER PUBLICATIONS

Bentley et al. The Use of Microcomputed Tomography to Study Microvasculature in Small Rodents; American Journal of Physiology, Regulatory, Integrative and Comparative Physiology, vol. 282 (2002) R1267-R1279.*
Cavanaugh et al. In Vivo Respiratory-Gated Micro-CT Imaging in Small Animal Oncology Models; Molecular Imaging, vol. 3, No. 1 (2004) pp. 55-62.*
Ritman, E. L. Molecular Imaging in Small Animals—Roles for Micro-CT; Journal of Cellular Biochemistry, Supplement 39 (2002) pp. 116-124.*
Watz et al. Micro-CT of the Human Lung: Imaging of Alveoli and Virtual Endoscopy of an Alveolar Duct in a Normal Lung and in a Lung With Centrilobular Emphysema—Initial Observations; Radiology, vol. 236 (2005) pp. 1053-1058.*
Ananda et al., "The visualization of hepatic vasculature by X-ray micro-computed tomography," *J. of Electron Microscopy*, 55 (3): 151-155, 2006.
Austin et al., "The knockout mouse project," *Nat. Genetic.*, 36: 921-924, 2004.
Bahadur and Keller, "Multimodality holder for co-registered anatomical and molecular small animal imaging," oral presentation to the scientific advisory committee of the University of Texas Health Science Center at San Antonio Technology Ventures Office, Oct. 14, 2005.
Bahadur et al., "Cost-effective, safe and stealth small animal imaging chamber for multimodality imaging," *Society of Molecular Imaging 5th Annual Meeting*, Hawaii, Sep. 2006.
Bahadur et al., "Multimodality chamber for coregistered anatomical and molecular imaging of small animals," *Lab. Anim.*, 36 (8): 29-35, 2007.
Bajcsy et al., "Three-dimensional volume reconstruction for extracellular matrix proteins in uveal melanoma from fluorescent confocal laser scanning microscope images," *J. Microsc.*, 221 (1): 30-45, 2006.
Bao et al., "Use of a surrogate marker (human secreted alkaline phosphatase) to monitor in vivo tumor growth and anticancer drug efficacy in ovarian cancer xenografts," *Gynecologic Oncology*, 78: 373-379, 2000.
Beckmann et al., "Three-dimensional imaging of nerve tissue by X-ray phase-contrast microtomography," *Biophys. J.*, 76: 98-102, 1999.

(Continued)

*Primary Examiner* — Rebecca Prouty
*Assistant Examiner* — Paul Martin
(74) *Attorney, Agent, or Firm* — Fulbright & Jaworski L.L.P.

(57) ABSTRACT

Processes for producing a microCT image for virtual histology using x-ray microscopic computed tomography are described along with processes for rapid and inexpensive high-throughput methods of high resolution imaging for screening an ex vivo embryo for phenotype using computed tomography imaging. Staining of particular components of specimens with one or more staining agents is described which contributes to high quality image generation and identification of anatomical structures as well as localization of molecular targets. Inventive animal and specimen holders are detailed which allow for reduced post-imaging processing of generated images. In particular, animal and specimen holders are provided which include a highly transparent bed or liner which separates the animal or specimen from a less transparent structure. A further animal holder is provided for placing and/or maintaining the animal in a desired position during an imaging procedure or multiple imaging procedures including a bed conforming to the animal's body.

30 Claims, 10 Drawing Sheets

OTHER PUBLICATIONS

Bezdek et al., "Review of MR imagine segmentation techniques using pattern recognition," *Am. Assoc. Phys. Med.*, 20 (4): 1033-1048, 1993.

Brown, "A survey of image registration techniques," *ACM Computing Surveys*, 24 (4): 325-376, 1992.

Capecchi, "Gene targeting in mice: functional analysis of the mammalian genome for the twenty-first century," *Nat. Rev. Genet.*, 6 (6): 507-512, 2005.

Cates et al., "Case study: an evaluation of user-assisted hierarchical watershed segmentation," *Med. Image Anal.*, 9 (6): 566-578, 2005.

Chaudhuri et al., "Blood-based screening and light based imaging for the early detection and monitoring of ovarian cancer xenografts," *Technology in Cancer Research and Treatment*, 2 (2): 171-179, 2003.

Chen et al., "Current progress of imaging screens at the mouse imaging centre," Integrated Functional Genomics of the Mouse Conference, Oct. 6-7, 2003, downloaded from http:www.cs.sfu.ca/~hamarneh/ecopy/ifgm2003.pdf.

Chow et al., "A method of image registration for small animal, multi-modality imaging," *Physics in Medicine and Biology*, 51: 379-390, 2006.

Christensen, "Deformable shape models for anatomy," dissertation, Washington University, St. Louis, United States, 1994.

Cockman et al., Quantitative imaging of proteoglycan in cartilage using a gadolinium probe and microCT, *Osteoarthritis Cartilage*, 14 (3): 210-214, 2005.

Cootes et al., "Anatomical statistical models and their role in future extraction," *Br. J. Radiol.*, 77 (Spec. No. 2): S133-S139, 2004.

Davidson et al. "Bioinformatics beyond sequence: mapping gene function in the embryo," *Nature Reviews Genetics*, 2: 409-417, 2001.

Gonzalez and Woods, "Image enhancement in the frequency domain," *Digital Image Processing*, 147-219, 2002.

Gooch et al., "A non-photorealistic lighting model for automatic technical illustration," *Proceedings of ACM Siggraph*, 447-452, 1998.

Hard and Butler, "Ultrastructural analysis of renal mesenchymal tumor induced in the rat by dimethylnitrosamine," *Cancer Research*, 31: 348-365, 1971.

Heinzer et al., "Hierarchical imaging of brainmicro-vasculature in a mouse model for Alzheimer's disease," 6th SLS Users' Meeting, Oct. 17-18, 2005; Poster session, abstract, downloaded from http://sls.web.psi.chi/view.php/users/affairs/umeetings/umee2005/heinzer.pdf.

International Search Report and Written Opinion, issued in PCT/US2007/02264, mailed Dec. 26, 2007.

Jacobs et al., "Towards a micro MRI atlas of mouse development," *Comput. Med. Imaging Graph*, 23 (1): 15-24, 1999.

Johnson et al., "High-throughput morphologic phenotyping of the mouse brain with magnetic resonance histology," *NeuroImage*, 2007.

Johnson et al., "Virtual histology of transgenic mouse embryos for high throughput phenotyping," *PLoS Genetics*, 2 (4): 61, 2006.

Joshi et al., "Multiscale deformable model segmentation and statiscal shape analysis using medical descriptions," *IEEE Transactions on Medical Imaging*, 21 (5): 807-832, 2002.

Keller et al., "Alveolar rhabdomyosarcomas in conditional Pax3:Fkhr mice: cooperativity of Ink4a/ARF and Trp53 loss of function," *Genes Dev.*, 18: 2614-2626, 2004.

Keller et al., "Pax3: fkhr interferes with embryonic Pax3 and Pax7 function: implications for alveolar rhabdomyosarcoma cell of origin," *Genes & Development*, 18: 2608-2613, 2004.

Keller, "Supplemental Data," oral presentation to the scientific advisory committee of the University of Texas Health Science Center at San Antonio Technology Ventures Office, Aug. 23, 2005.

Keller, "Virtual histology for rapid embryo phenotyping," slides from oral presentation to TVO Committee, Children's Cancer Research Institute at the University of Texas Health Science Center, San Antonio, Sep. 2005.

Keller, Charles Keller's adaptation of the official Anne Boulet—Vector Labs Protocol for "Whole mount IHC in situ analysis of mouse embryos," Sep. 8, 2003.

Keller, Charles Keller's adaptation of the official Ben Arenkiel Protocol for "X-gal staining of mouse embryos and adult mouse tissues," Sep. 28, 2003.

Kindlemann et al., "Curvature-based transfer functions for direct volume rendering: methods and applications," *IEEE Visualization*, 513-520, 2003.

Kniss et al., "Multidimensional transfer functions for volume rendering," *The Visualization Handbook*, eds. Hansene and Johnson, 189-210, 2005.

Levoy, "Display of surfaces from volume data," *IEEE Computer Graphics and Applications*, 8: 29-37, 1988.

Lyons et al., "The generation of a conditional reporter that enables bioluminescence imaging of Cre/loxP-dependent tumorigenesis in mice," *Cancer Research*, 63: 7042-7046, 2003.

Maintz and Viergever, "A survey of medical image registration," *Med. Im. Anal.*, 2 (1): 1-36, 1998.

Mangan and Whitaker, "Partitioning 3D surface meshes using watershed segmentation," *IEEE Trans. Vis. Comput. Graph.*, 5: .308-321, 1999.

Maronpot et al., "Applications of magnetic resonance microscopy," *Toxicol. Pathology*, 32 (2): 42-48, 2004.

Mayo et al., "X-ray phase-contrast microscopy and microtomography," *Optics Express*, 11 (19): 2289-2302, 2003.

McInerney et al., "Deformable models in medical imaging analysis: a survey," *Med. Image Anal.*, 1 (2): 91-108, 1996.

Miller et al., "Statistical methods of computation anatomy," *Statistical Methods in Medical Research*, 6: 267-299, 1997.

Morenko et al., "In vivo micro computed tomography of subchondral bone in the rat after intra-articular administration of monosodium iodoacetate," *Contemp. Top. Lab Anim. Sci.*, 43 (1): 39-43, 2004.

Nilsson et al., "An in vivo mouse report gene (human secreted alkaline phosphatase) model to monitor ovarian tumor growth to therapeutics," *Cancer Cemoter. Pharmacol.*, 49: 93-100, 2002.

Nozawa et al., "Infiltrating neutrophils mediate the initial angiogenic switch in a mosue model of multistage carcinogenesis," *PNAS USA*, 103 (33): 12493-12498, 2006.

Office Action, issued in U.S. Appl. No. 11/888,995, filed Aug. 3, 2007.

Osada et al., "Shape distributions," *ACM Computing Surveys*, 21 (4): 807-832, 2002.

Parton, "Ultrastructural localization of gangliosides; $GM_1$ is concentrated in caveolae," *J. Histochem. Cytochem.*, 42 (2): 155-166, 1994.

Pham et al., "Current methods in medical image segmentation," *Annu. Rev. Biomed. Engl.*, 2: 315-337, 2000.

Pivovarov et al., "MIPortal: a high capacity server for molecular imaging research," *Mol. Imaging*, 4 (4): 425-431, 2005.

Pullen et al., "Human embryology digital library and collaboratory support tools," *George Mason University*, 2003.

Rosenthal et al., "Rapid high resolution three dimensional reconstruction of embryos with episcopic fluorescence image capture," *Birth Defects Res C Embryo Today*, 72: 213-223, 2004.

Safran et al., "Mouse reporter strain for noninvasive bioluminescent imaging of cells that have undergone Cre-mediated recombination," *Molecular Imaging*, 2 (4): 297-302, 2003.

Sakai et al., "Addition of phosphotungstic acid to ethanol for dehydration improves both the ultrastructure and antigenicity of pituitary tissue embedded in LR white acrylic resin," *Arch. Histol. Cytol.*, 68 (5): 337-347, 2005.

Smith et al., "Magnetic resonance microscopy of mouse embryos," *PNAS USA*, 91: 3530-3533, 1994.

Uhrbom et al., "Dissecting tumor maintenance requirements using bioluminescence imaging of cell proliferation in a mouse glioma model," *Nature Medicine*, 10 (11): 1257-1260, 2004.

* cited by examiner

Figure 8 (A-C)
8A
8B
8C

Figure 9 (A-B)
9A
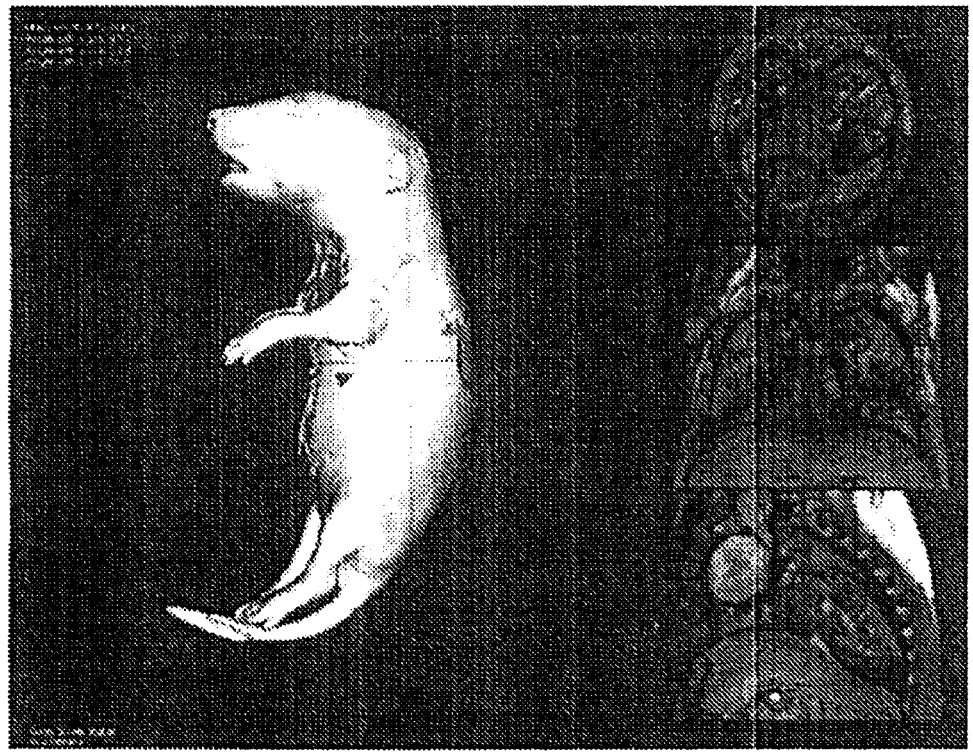
9B
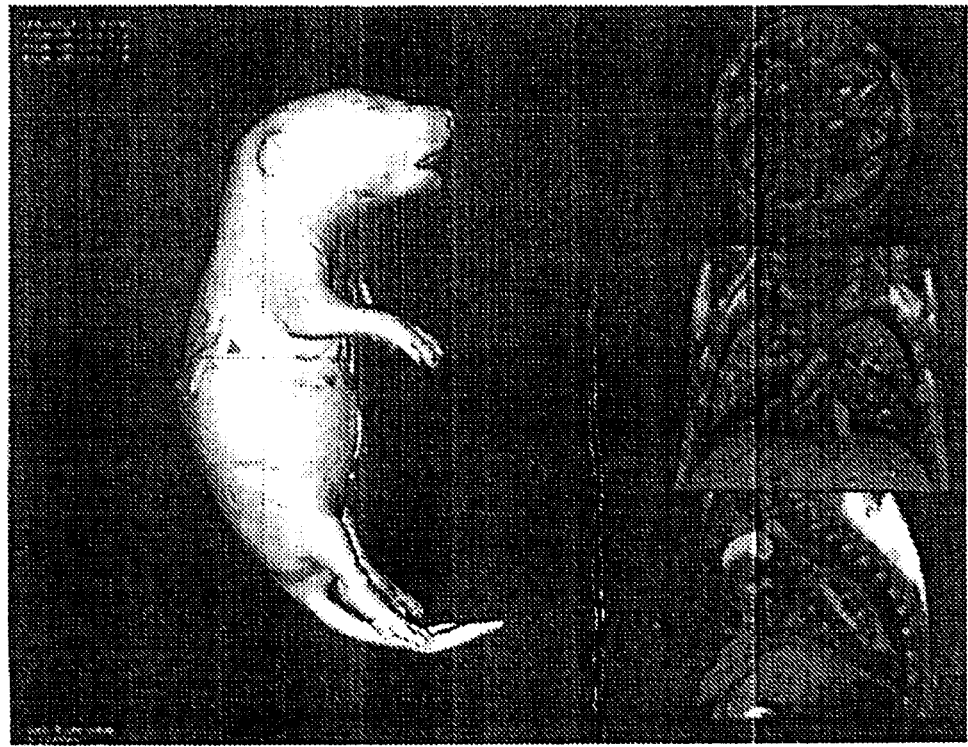

Figure 9 (C-D)
9C
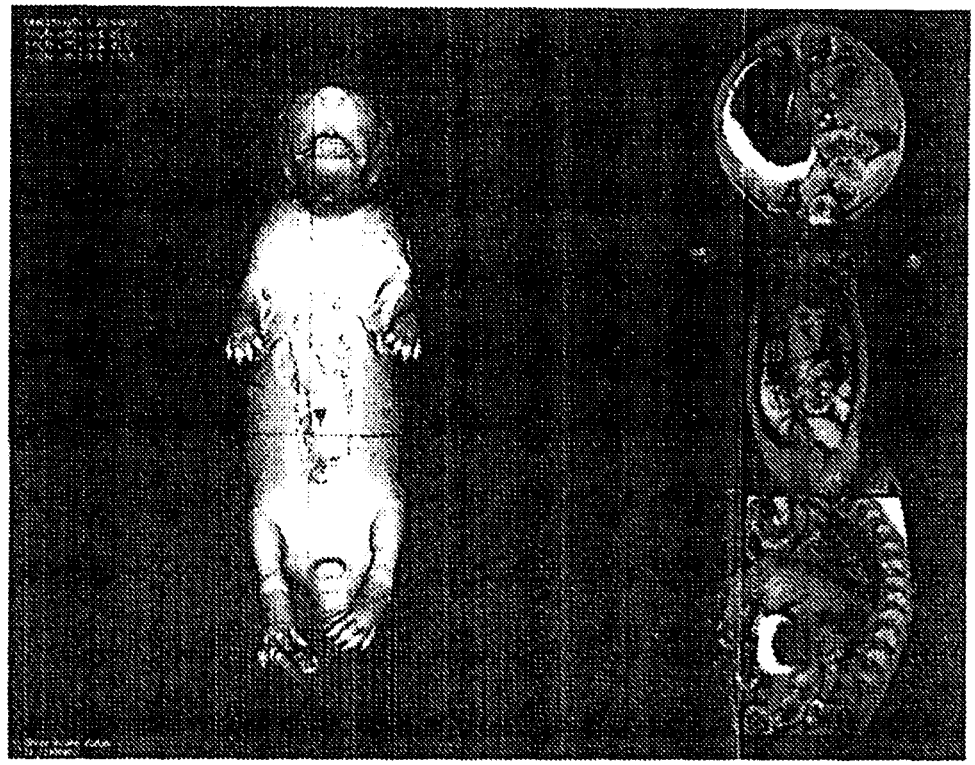
9D
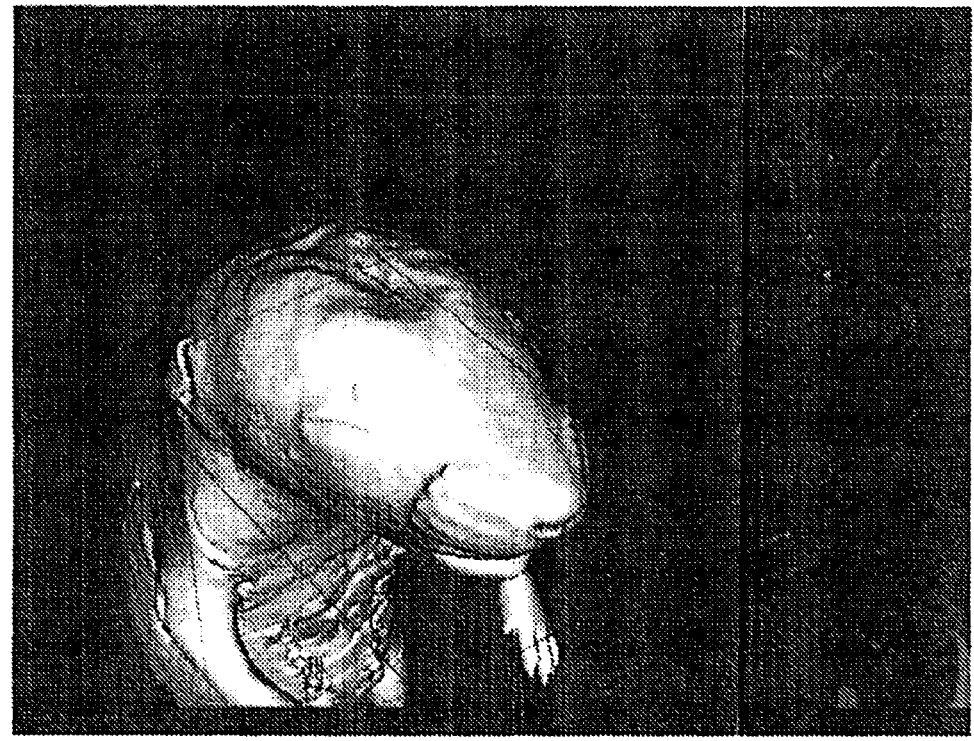

Figure 10 (A-E)
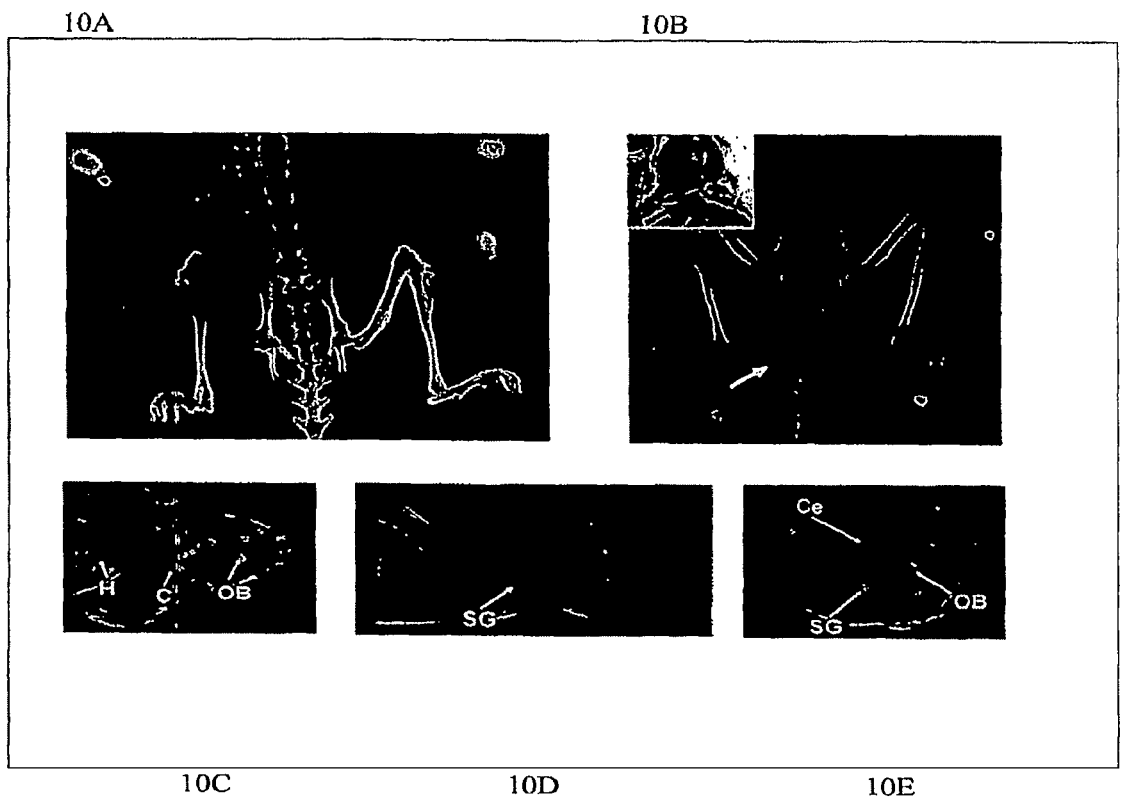

Figure 11 (A-D)
11A (top)
11B (middle)
11C (bottom left)
11D (bottom right)
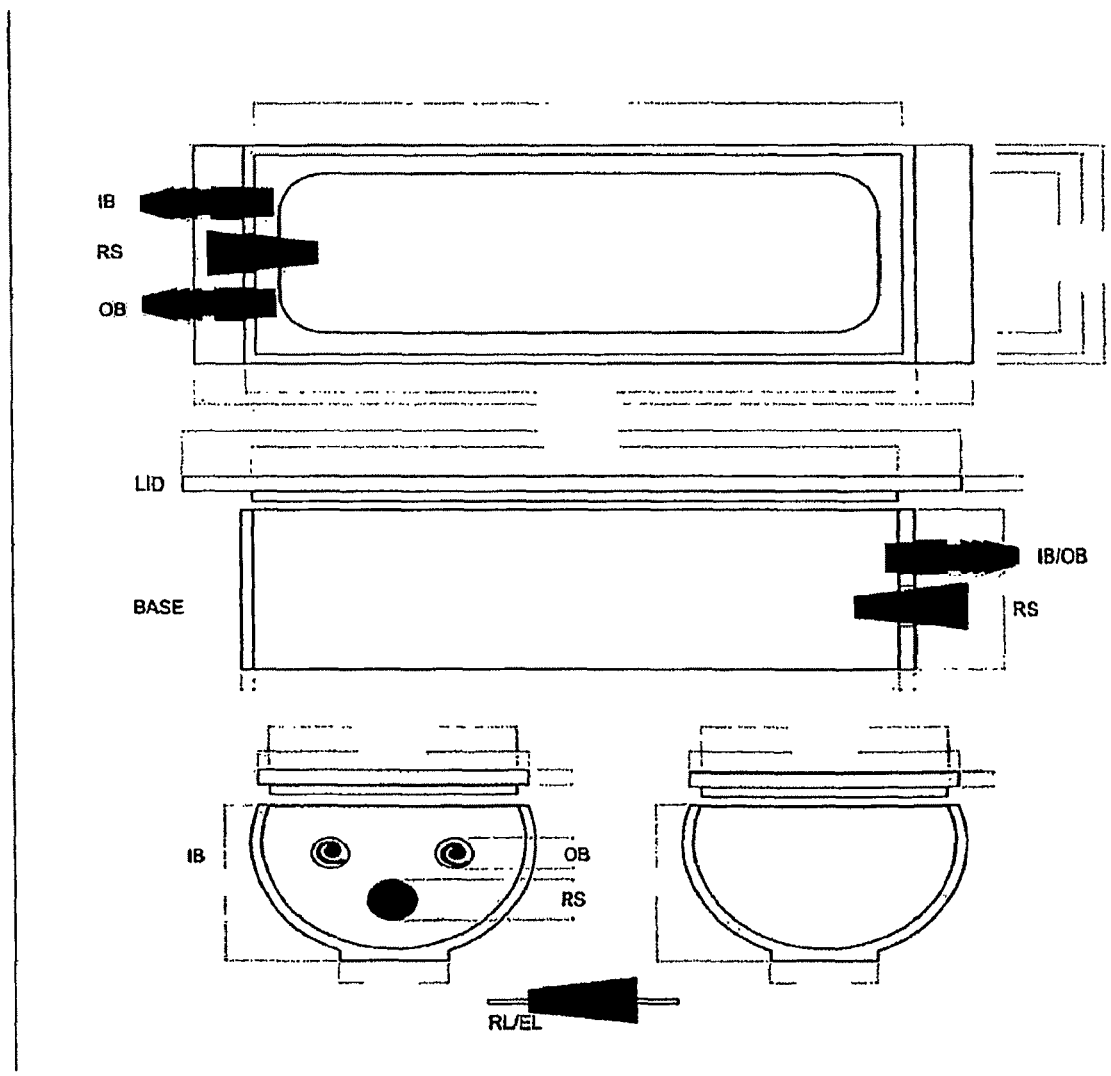

Figure 12 (A-E)
12A (top left); 12B (top right); 12C (middle); 12D (bottom left); 12E (bottom right)
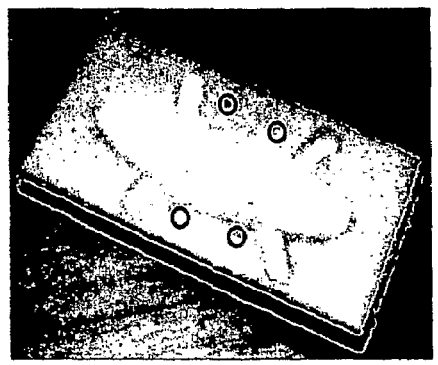
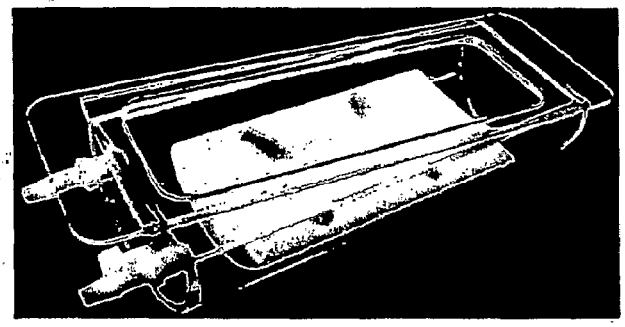
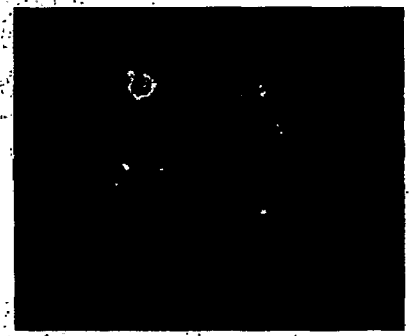

PROCESS AND APPARATUS FOR MICROCT IMAGING OF EX VIVO SPECIMENS

RELATED APPLICATIONS

This application is a non-provisional application that claims priority benefit of U.S. Provisional application Ser. No. 60/762,327 filed Jan. 26, 2006; the contents of which are incorporated herein by reference.

FIELD OF THE INVENTION

The present invention relates in general to compositions, processes and apparatus for imaging, and in particular to improved preparation, collection and processing of specimen images, especially those obtained from X-ray microscopic computed tomography.

BACKGROUND OF THE INVENTION

Developments in imaging technologies have traditionally contributed to breakthroughs in scientific understanding. While the earliest imaging tools were primarily directed to resolving gross anatomical structures, modern imaging techniques allow visualization of very fine structural details as well as molecular information in some cases.

The development of a number of new imaging modalities, along with evolution of molecular and cellular biology techniques, has created a need for improved methods and devices to maximize the advantages offered by these technologies. For example, genetically modified animals are readily produced by molecular biology methods. Systematic imaging of genetically modified animals offers an opportunity to add significantly to an understanding of the function of particular genes. Additionally, it is now feasible to spatially correlate data from various imaging modalities, in order to glean still further information from genetically modified animals, as well as other animals and specimens. Imaging techniques amenable to correlation illustratively include confocal optical microscopy (COM), positron emission tomography (PET), magnetic resonance imaging (MRI), X-ray computed tomography (CT), and single photon emission computed tomography (SPECT). However, in spite of the opportunities presented, there remain limitations in imaging technologies.

While gene targeting potentially allows unprecedented insight into the function of genes and their roles in patterning the mammalian embryo (Capecchi, M. R., Nat Rev Genet. 6, 507-12, 2005), the number of animals which must be imaged in such a project is large. A full understanding of mammalian development by this means, using the gene targeting approach for every one of the ~25,000 or more mouse genes, may seem like a daunting task. Nevertheless, more than ten percent of known mouse genes have already undergone disruption by gene targeting, while the National Institutes of Health is leading an effort to create a collection of mouse lines with disruption of every known gene (Austin, C. P. et al., Nat Genet 36, 921-4, 2004). The challenge laid before developmental biologists will be to systematically analyze morphological phenotypes, and where possible, determine the quantitative contribution of each gene to patterning of the embryo. Attributes associated with an imaging tool for this type of phenomic analysis include rapid scan speed, low-cost, and accessible high-throughput methods of high resolution anatomical imaging as well as stage-specific, statistically-averaged wild type morphological atlases that can be used to discern normal variation from mutant phenotype (Jacobs, R. E., et al., Comput Med Imaging Graph 23, 15-24, 1999). Traditional histological methods of screening embryonic animals or other specimens for anatomical and/or molecular variation are time intensive, such that processing and analysis of large numbers of specimens is generally impractical.

Pre-clinical studies are also becoming increasingly reliant on multiple imaging modalities for sophisticated evaluation of various parameters to allow for accurate and largely non-invasive assessment and/or monitoring of phenotype resulting from various stressors such as mutation, tumor size and growth rate, effect of drug or other treatment, and drug localization. This effort is frustrated by multiple mode imaging owing to difficulties in attaining image registration due to positioning inconsistency. Currently, animals tend to move over time in a holder and often, the animal must be moved to a different holder to accommodate the particularities of various imaging techniques.

A limitation of existing animal holders is that close contact of the animal with the animal holder is visible in the resulting images, making image post-processing tedious. An image of animal tissues in proximity with the holder is often obscured or poorly resolved. Image quality and efficiency suffer since the holder must be identified and subtracted in subsequent image processing. To date, an animal holder for acquisition of microCT images has not been identified that mitigates the shortcomings of existing holders, allowing the specimen to be distinguished clearly from the holder.

X-ray microscopic computed tomography (microCT) represents an attractive imaging choice, alone or as part of an imaging battery, owing to the suitability of the technique to semi-automated or fully automated methods of analysis. This attribute is important in achieving high-throughput phenomic studies or clinical pathology results. A comparison of CT and magnetic resonance methods, applications, and costs shows that microCT-based virtual histology offers a potentially higher resolution mode of morphometrics that is simple to implement, relatively inexpensive, and more rapid than comparable methods of phenotyping embryo anatomy.

MicroCT virtual histology would be an even more attractive imaging technique if limitations associated with specimen staining and mounting could be overcome. Current staining processes, such as that described in M. D. Bentley et al., National Synchotron Light Source Activity Report 1998 Beamline X2B, struggle to yield an adequate signal to noise ratio in order to achieve high resolution of anatomical structures. MicroCT virtual histology throughput has also been hampered by a lack of specimen holders capable of containing multiple specimens. In addition, microCT virtual histology of whole embryos results in voluminous data. The true value of such data will only be fulfilled if systems and methods for retrievably storing and analyzing data are developed.

Thus, there is a continuing need for improved staining processes for producing a microCT image, systems and processes for retrievably storing and analyzing such image data, and specialized devices for holding a stained specimen or living animal to be imaged using one or more imaging modalities in order to take advantage of these opportunities.

SUMMARY OF THE INVENTION

Virtual histology, using imaging of selectively stained samples, provides an attractive alternative or supplement to conventional histology for the detection of alterations, mutations, injuries or other perturbations of tissues, including spontaneous and directed mutations.

The present invention provides improved stains and staining procedures for preparing specimens, e.g., biological specimens, for image acquisition in virtual histology and other applications. Improved systems and processes for retrievably storing and analyzing image data acquired from stained specimens are also provided. Specialized devices for holding a stained specimen or living animal to be imaged are provided according to embodiments of the present invention.

A process of producing a microCT image is provided which includes incubating a specimen in a first staining composition containing a first staining agent, to produce a stained specimen. The stained specimen is then scanned in an X-ray computed tomography scanner to produce a microCT image. It is generally preferred that, following staining, the stained specimen is transferred into a liquid medium having a density that is less than that of the tissue. The tissue is fully or partially surrounded by the liquid medium of lower density and is optionally suspended in this medium.

An inventive process optionally further includes exposing the stained specimen to a second staining agent to produce a double-stained specimen. The second staining agent may be present in the first staining composition or in a second staining composition.

Staining compositions optionally include an organic fixative, such as glutaraldehyde and formaldehyde, and/or a buffer.

The first staining agent or second staining agent preferably includes about 0.1-1.25 weight percent osmium tetroxide. A cacodylate buffer is also used to great effect as a component of the first or second staining composition. Further exemplary staining agents include: ethidium bromide acid, cis-platinum, uranyl acetate, phosphotungstic acid, phosphomolybdic acid, ammonium molybdate, silver salts, and sodium uranate.

A staining agent stains or is indicative of one or more of a variety of cell and/or tissue components such as a cell and/or organelle membrane, a nucleus, a particular molecule, such as a reporter gene-product, or a particular molecule type, such as protein, lipid or carbohydrate.

In a detailed process, the specimen to be scanned is a specimen obtained from an individual animal at a first time. Later, a second specimen is obtained from the same individual animal at a second time. Both the first and second specimens are stained and scanned to produce a microCT image. In general, a procedure is performed subsequent to the first time a specimen is obtained and prior to obtaining the second specimen. In this way, the procedure may be assessed for effectiveness or other effects.

An inventive process for screening an ex vivo embryo for phenotype is described according to the present invention which includes incubating an ex vivo embryo in a first staining composition to produce a stained ex vivo embryo. The stained ex vivo embryo is scanned in an X-ray computed tomography scanner to produce a microCT image of the stained ex vivo embryo. A microCT image or images of the stained ex vivo embryo is compared to computed tomography image or images of a statistically-averaged, age-matched atlas of a control ex vivo embryo to determine differences between the images, to determine the phenotype of the ex vivo embryo. A micro CT image of the ex vivo embryo may include an isosurface rendering of the ex vivo embryo. Further, the micro CT image of the ex vivo embryo may include a virtual section of the ex vivo embryo.

Multiple specimens, such as multiple embryos may be scanned in an inventive process.

A process for screening an ex vivo fetus for phenotype is provided that includes blanching, skinning, and incision of the ex vivo fetus. The processed fetus is then incubated in a first staining composition to form a stained ex vivo fetus. The stained ex vivo fetus is scanned by an X-ray computed tomography scanner to produce a microCT image of the stained ex viva fetus. Any downstream image analysis procedures are similar to those for the screening of ex vivo embryo.

An inventive process for screening a tissue section is described according to the present invention which includes precise cutting of a tissue to form a tissue section with certain thickness. The tissue section is then subject to staining with a staining agent of a concentration that is customized to the thickness of the tissue section. The scanning and image analysis are similar to those for the screening of ex vivo embryo.

A specimen holder for use in X-ray computed tomography, is detailed which includes a multi-chamber specimen holder, each chamber having a wall having a support portion for support of a specimen placed in the chamber. A liner is provided which contacts the specimen to prevent contact of the specimen with the wall. At least a portion of the liner in contact with the specimen is highly transparent to electromagnetic radiation used to produce a microCT image. Exemplary specimen holders are multiple chamber specimen holders.

A commercial package for use in a process of producing a microCT image of multiple specimens is provided which includes a multi-chamber specimen holder wherein the chambers are each separated by a wall. Liners are provided for contacting a specimen placed in a chamber of the specimen holder and separating the specimen from contact with the wall of a chamber. At least a portion of the liner in contact with the specimen is highly transparent to electromagnetic radiation used to produce a microCT image.

A computer-based process for collecting, storing and retrieving microCT images is detailed which includes generating a digital micro CT image, electronically transmitting the image to a centralized data storage location associated with a computer, retrieving the image from the storage location in response to a request; and electronically displaying or transmitting the image to a second location in response to the request.

Further provided is an animal holder for use in an imaging process which includes a wall having a support portion for supporting an animal. A bed for an animal to be imaged is placed on the support portion of the wall. At least the portion of the bed surface which contacts the animal, and optionally a portion of the thickness adjacent to the portion of the bed surface which contacts the animal are highly transparent and non-reflective to electromagnetic radiation used in the imaging process.

An animal holder is also provided for supporting an animal and maintaining the animal under inhaled anesthesia in an ergonomic, reproducible, and results-oriented position. Such an animal holder includes a wall having a support portion for supporting the animal. A bed placed on the support portion of the wall includes a portion adapted to conform to at least a part of the animal so as to support the animal and maintain the animal in a desired and reproducible position during an imaging procedure.

Preferably, at least a portion of the animal holder is substantially transparent to electromagnetic radiation used in the imaging process so that the radiation is minimally attenuated and passes through the holder producing a minimal or no image of the holder itself.

Other objects, aspects and advantages of the present invention will be apparent from the detailed description that follows.

BRIEF DESCRIPTION OF THE DRAWINGS

FIG. 8 shows morphological changes of a fetus just after being freshly euthanized (A), then after being blanched (B), and then after being skinned (C) in accordance with the present invention.

FIG. 9 illustrates physical sites on a fetus where incisions are made to enhance staining penetration. 9A and 9B show alternative incisions made to the thoracic pleura; 9C shows an incision made to the peritoneum; 9D shows an incision made to the dura matter.

FIG. 10 illustrates exemplary successful co-registration between two datasets. FIG. 10A shows that of microCT and luminescent optical imaging datasets; FIG. 10B shows that of microCT and near-infrared fluorescence optical imaging datasets; FIGS. 10C-10E show that of MRI and MicroPET imaging systems.

FIG. 11 illustrates orthographic views of an inventive animal holder with three hose barbs (1/4"-5/16") with 11A showing a top view, 11B showing a side view, 11C showing a front view, and 11D showing a rear view.

FIG. 12 depicts a customized disposable bed made of low density but rigid form which aids in reproducible positioning of an animal during an imaging procedure (12A); fiducial markers visible with microPET/microMRI/microCT/Optical used as reference points to co-register data from different modalities (12B); a foam bed positioned with an inventive animal holder according to the present invention (12C); and an inventive holder with an animal bed removable from the holder (12E) which enables the separation of the bed and the holder as compared to a conventional animal holder which does not (12D).

DETAILED DESCRIPTION OF THE INVENTION

Figure 1:
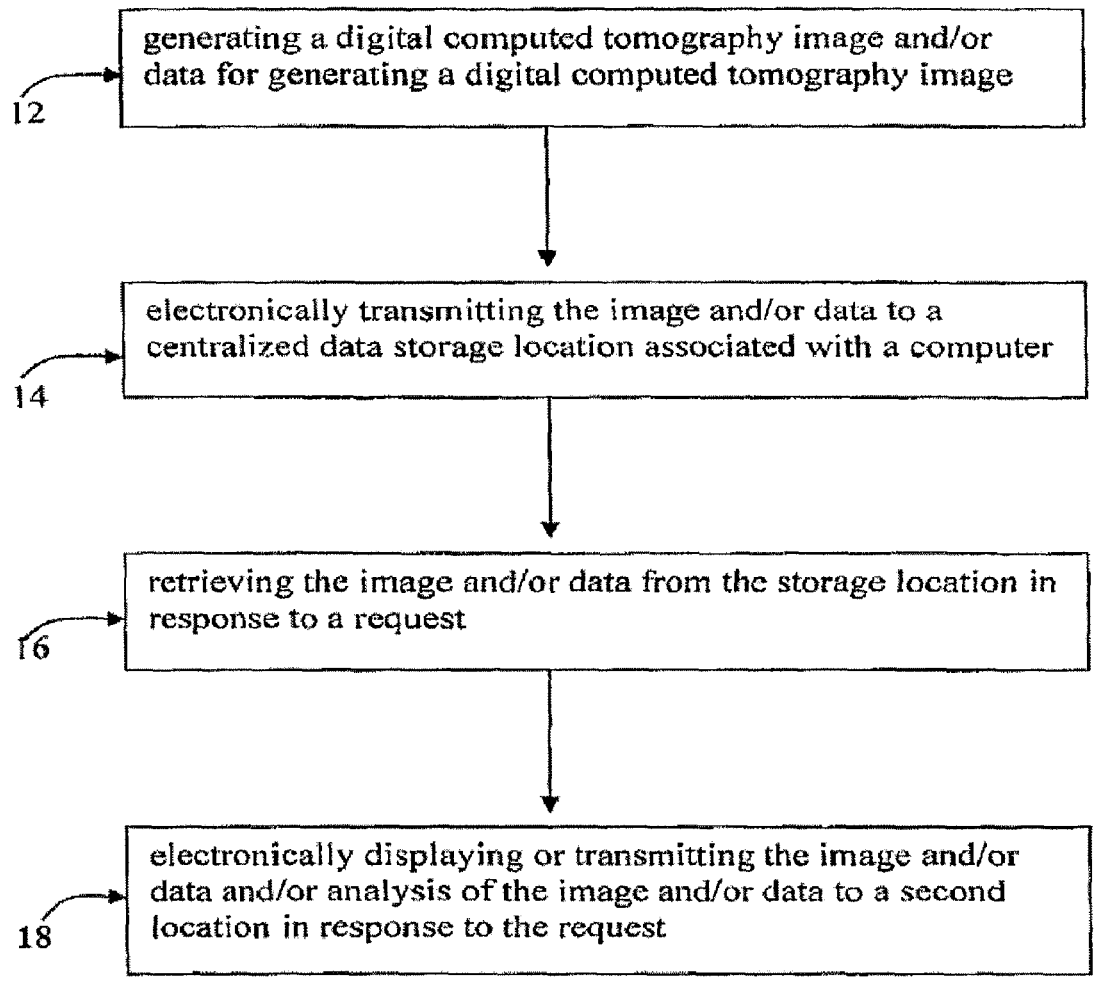
FIG. 1 illustrates an inventive computer-based process for collecting, storing and retrieving micro CT images.

The present invention provides compositions, devices, processes, and methods of use in the preparation of samples for imaging and acquisition of images of those specimens. Exemplar specimens include biological specimens (e.g., tissues, embryos). In an exemplary embodiment, images of the specimens are acquired utilizing an X-ray imaging modality, e.g., microCT.

In one embodiment, the imaging modalities of the present invention, e.g., microCT, allow high resolution, non-destructive analysis of the status, integrity and development of biological tissues in a wide variety of animal models and disease conditions. The sensitivity and specificity of microCT-based analyses accurately detects and assesses both gross and subtle changes in disease states and animal models. This new technology provides a rapid and inexpensive method that enhances visualization and analysis of complex global 3-dimensional organization. Unlike traditional histology, which requires meticulous slicing and individual examination, this new technique includes staining tissues (e.g., intact fetuses) with specific dyes and scanning them with microscopic computed tomography (microCT).

The method produces datasets of the whole specimen providing a digital visualization with capabilities of taking a number of measurements, e.g., distance, area, and volume. This inherently digital method provides a practical tool for fields as diverse as reproductive toxicology and Knockout or Transgenic animal phenotyping.

Accordingly, the present invention has utility in the preparation of specimens for acquisition of images, and collection, and processing of specimen images. In particular, the images are collected with X-ray microscopic computed tomography (microCT).

Improved stains and staining processes for processing a specimen for imaging are provided. Thus, the present invention provides a staining composition that includes an electron dense staining agent, optionally combined with a buffer and/or a fixative and/or across-linking agent and/or a reporter substrate for a reporter gene product.

Also provide are methods for treating a specimen with the stains of the invention and other stains to provide images of specimens superior to those produced using currently recognized stains and/or staining techniques.

The present invention also provides a method for producing a micro CT image, systems and processes for retrievably storing and analyzing such CT image data, and specialized devices for holding a stained specimen or living animal to be imaged using one or more imaging modalities are provided according to embodiments of the present invention.

A process of obtaining virtual histology images using microCT is also provided. This technique permits specimens, e.g., animals and tissues, to be scanned at high resolution in comparable or less time and at a fraction of the expense of magnetic resonance microscopy. High resolution images are possible using the disclosed processes for microCT. In an exemplary embodiment, the methods provide for resolutions of at least about 6-200 microns.

An inventive process may be used to phenotype transgenic or other types of mutant specimens, including whole animals and tissues isolated from these animals. Clinical applications include evaluation of biopsy specimens and assessment of efficacy of a particular medical treatment or intervention. Inventive processes also find use in assessing toxicity of proposed new drugs or other substances on animals, and especially on embryonic animals. An inventive process may also be useful in the high-throughput evaluation of teratogenic effects of medications, evaluation of tissues from adult animals, and neocapillary mapping for tumor biopsies of patients undergoing anti-angiogenesis therapies, for example.

For increased throughput of these types of studies, multiple specimens are optionally scanned simultaneously or nearly simultaneously in the same field of view.

A process of producing a micro CT image is provided according to the present invention which includes incubating a specimen in a staining composition to produce a stained specimen and scanning the specimen in an X-ray computed tomography scanner to produce a micro CT image.

The Stains

In an exemplary embodiment, the invention provides a stain of use in preparing specimens acquisition of images, such as microCT images. An exemplary staining composition includes an electron dense staining agent which produces an electron dense staining of one or more components of an animal cell or tissue. A currently preferred electron dense staining agent is a species that includes a metal atom or ion.

Exemplary staining agents include metals such as osmium (e.g., osmium tetroxide), tungsten (e.g., phosphotungstic acid, sodium tungstate), molybdenum (e.g., ammonium molybdate, phosphomolybdic acid), the noble metals, e.g., (platinum (e.g., cisplatin), gold (e.g., sodium chloroaurate)), bismuth (e.g., bismuth subnitrate), cadmium (e.g., cadmium iodide), iron (e.g., ferric chloride, potassium ferricyanide, potassium ferrocyanide), indium (e.g., indium trichloride), lanthanum (e.g., lanthanum trichloride), lead (e.g., lead acetate, lead citrate, lead nitrate), ruthenium (e.g., ruthenium red), silver (silver nitrate, silver proteinate, silver tetraphenylporphyrhin), thalium (e.g., thallium nitrate), uranium (e.g., uranyl acetate, uranyl nitrate) and vanadium (vanadyl sulfate). Other appropriate metals of use in the methods of the invention will be apparent to those of skill in the art.

Organic stains are also of use in the staining compositions of the present invention. An exemplary organic stain is ethidium bromide.

The staining agent is present in the staining composition in any concentration useful to provide a desired level of contrast in the image of the specimen. Appropriate concentrations of a selected staining agent are readily determinable by those of skill in the art without resort to undue experimentation. For example, arrays of staining compositions including a single staining agent are prepared. Each composition is used to stain a specimen. The level of staining of each specimen by each staining composition is determined by acquiring a microCT image of each of the stained specimens.

In an exemplary embodiment, the staining agent is present in the staining composition in an amount from about 0.01 weight percent to about 10 weight percent, preferably from about 0.1 weight percent to about 5 weight percent, more preferably from about 1 weight percent to about 3 weight percent.

Optionally, the staining agent is included in a staining composition which further includes a buffer. The buffer is present in any concentration that is useful to provide a desired level of staining of the specimen, as evidenced, in one embodiment, by obtaining a desired level of contrast in a microCT image of the stained tissue. A buffer which has a different osmotic concentration than the tissue is optionally used in the process of stain penetration so as to accelerate transfer of stain molecules into components of the tissue, e.g., tissue cells.

Exemplary buffer concentrations for staining compositions of the invention range from about 0.01M to about 1M. A generally preferred buffer concentration range is from about 0.1M to about 0.5M.

A preferred buffer is a cacodylate buffer, e.g., sodium, cacodylate trihydrate.

Further optionally, the staining composition includes a fixative or cross-linking agent such as glutaraldehyde, formaldehyde, alcohols, or a combination of these. In representative staining compositions, the fixative or cross-linking agent is present in a concentration range of from about 0.05% to about 5%, preferably from about 0.1% to about 3% and more preferably from about 1% to about 1.5%.

The staining composition may also include a tissue penetration enhancing agent. A representative tissue penetration enhancing agent is DMSO.

In another exemplary embodiment, the staining composition includes both the staining agent and a species that is indicative or confirmative of the presence of a reporter gene through direct interaction with that gene or with a product of the reporter gene. In a preferred embodiment, the reporter gene product forms a complex with the species recited above and the staining agent. The resulting agent is detectable by an imaging modality, e.g., an X-ray imaging modality, such as microCT.

In a preferred embodiment, the staining agent includes osmium tetroxide, and preferably includes about 0.1-4 weight percent osmium tetroxide. Further preferred are concentrations in the range of about 0.1-1.84 weight percent osmium tetroxide. Also preferred are concentrations in the range of about 0.5-1 weight percent osmium tetroxide. Preferred concentrations of osmium tetroxide produce high quality images, due at least in part to decreased background and a larger range of signal intensity.

In a preferred embodiment in which the staining agent is osmium tetroxide, the staining composition further includes a fixative or cross-linking agent. Preferred concentrations of the fixative or cross-linking agent are from about 0.01% to about 3%, more preferably from about 0.1% to about 1%. A presently preferred fixative or cross-linking agent is glutaraldehyde. This same preferred embodiment includes a buffer at a concentration of from about 0.05M to about 0.5M, more preferably from about 0.08M to about 0.2M. A presently preferred buffer includes arsenic, e.g. cacodylate.

An alternate preferred staining agent is phosphotungstic acid (PTA), and preferably includes from about 3 to about 10 weight percent PTA. Further preferred are concentrations in the range of from about 4 to about 6 weight percent PTA. Also preferred are concentrations in the range of from about 4.8 to about 5.2 weight percent PTA. Preferred concentrations of PTA produce high quality images, due at least in part to increased signal/background ratio and hence a larger dynamic signal intensity.

Methods

As set forth hereinabove, the present invention also provides methods of staining specimens and acquiring and processing images of the stained specimens. The following sections detail selected exemplary embodiments of these methods of the invention.

In an exemplary embodiment, the specimen is incubated for a selected period in a staining composition, which is optionally a staining composition of the invention. The period for which the specimen is incubated with the staining composition is readily determined by those of skill in the art and is informed by the level of contrast desired in the images acquired from the stained specimen.

It is generally preferred that the specimen remain in contact with the staining composition for a period of at least about 1 hour. Periods of at least about 3 hours, at least about 6 hours and at least about 12 hours are also of use in the methods of the invention.

Following its contact with the staining composition, the specimen (now a stained specimen) is optionally contacted with a buffer which has a different osmolarity than that of the tissue to accelerate or otherwise enhance the transfer of stain molecules into components of the specimen, e.g., tissue cells. An exemplary buffer is a buffered saline solution, e.g., phosphate buffered saline. When this subsequent osmolarity differential is applied, the staining composition can be of a greater or lesser osmolarity than the buffer to which the stained specimen is subsequently submitted.

In yet another preferred embodiment, the stained specimen is further submitted to treatment with an organic solvent or a mixture of an organic solvent in water. Exemplary organic solvents are those that are at least partially soluble in water and include, e.g., alcohols, ethers, esters and the like. The medium in which the specimen is suspended can be altered from a first mixture (e.g., the staining composition) to a final mixture (e.g., 100% organic solvent) in a single step or, alternatively, the change in specimen environment can be accomplished by submitting the stained specimen to a gradient of medium compositions, moving step-wise or continuously from the first mixture to the final mixture.

The methods of the invention preferably provide stained specimens in which the density of the staining is essentially invariant from one border of the specimen to an antipodal border of the specimen. As used herein, the term "essentially invariant" refers to the homogeneity of the staining of a specimen. In a preferred embodiment, a specimen exhibiting essentially invariant staining will have a density of stain that varies by more than about 20%, more preferably by no more than about 10% and still more preferably by more than about 5% across a line through the specimen from a point on one border of the specimen to the antipodal point on the opposite border of the specimen.

In an exemplary method of the invention, a "solid tissue" is stained. As used herein, "solid tissue" refers to those tissues in which the parenchyma is present in an amount of at least about 50%. Solid tissue is distinct from tissue such as lung tissue.

In a particularly preferred embodiment, the methods of the invention provide a stained specimen, which is a solid tissue in which the density of the staining is essentially invariant. A preferred specimen is a whole organism, e.g., an embryo or fetus.

In another preferred embodiment, the specimen is sectioned or microtomed into slices of a thickness from about 4 mm to about 60 mm, more preferably from about 7 mm to about 40 mm. It is generally preferred that such tissue sections be solid tissue. Also, it is preferred that the density of staining of such specimens is characterizable as essentially invariant.

In a further exemplary embodiment, the penetration of the stain into specimen is enhanced prior to or during treatment of the specimen with the stain. In an exemplary method, the porosity of the specimen is enhanced by chemical or physical methods. Exemplary chemical methods include osmotic disruption of the integrity of the specimen structure and treatment of the tissue with a penetration enhancing substance, e.g., DMSO. Physical means include, but are not limited to puncturing the specimen to form channels in the specimen through which the stain flows with greater facility than through corresponding undisrupted regions of the specimen. Channels can be formed in the specimen by puncturing it with an object or by subjecting it to focused energy, such as the light from a laser.

In a general example of a staining process of the invention, a specimen, e.g., a cell, a tissue, an embryo, or a fetus, is stained to saturation for a selected period in a solution of 0.1 M buffer (pH 7.2), 1% fixative or cross-linking agent, and 1% staining agent, rocking at room temperature. The stained specimen is then washed and dehydrated. For example, specimens are washed for 30 minutes in 0.1M buffer, and twice more for 30 minutes in a second buffer providing an environment with an osmolarity different from the staining solution and/or the washing buffer subsequent to the staining solution. Specimens are then incubated in a graded series of organic solvent concentrations to 100% organic solvent prior to imaging. An organic solvent is an example of a medium that increases the apparent density differences between the suspension medium and the stained tissue.

In an exemplary staining process of the invention, a specimen, e.g., a cell, a tissue, an embryo, or a fetus, is stained to saturation overnight in a solution of 0.1 M sodium cacodylate (pH 7.2), 1% glutaraldehyde, and 1% osmium tetroxide, rocking at room temperature. Specimen The stained specimen is then washed and dehydrated. For example, specimens are washed for 30 minutes in 0.1M sodium cacodylate buffer, and twice more for 30 minutes in phosphate-buffered saline. Specimens are then incubated in a graded series of ethanol concentrations to 100% ethanol prior to scanning. Ethanol is an example of a medium that increases the apparent density differences between the suspension medium and the stained tissue.

In an exemplary embodiment, the specimen is a whole fetus. For the staining of a fetus, the fetus is optionally first blanched and skinned before staining. The fetus is dissected and removed of amnion and inner thin serosa membrane. A shallow cut is made on the ventral and dorsal sides of the fetus before the cut fetus is placed in a beaker filled with boiling water. The blanched fetus is then removed of epidermis/dermis. Additionally, several incisions are made on the skinned fetus to enhance stain penetration. Incisions are made external to the fetus, and preferably in the directions of lateral, supracostal, and vertical. The areas to be cut include, but are not limited to, the thoracic pleura, the peritoneum, and the dura matter.

In an exemplary embodiment, for the staining of a tissue other than embryo or fetus, the tissue is first cut to ensure a certain thickness. When osmium tetroxide is used as a staining agent, a staining solution containing osmium tetroxide in the range of 0.8 to 1.5 weight percent is preferred for staining a tissue section with a thickness <2 mm; a staining solution containing osmium tetroxide in the range of 1.5 to 2.2 percent solution weight is preferred for staining a tissue section with a thickness >2 mm to speed or otherwise enhance stain penetration of the section thickness.

A process according to the present invention may further include exposing the specimen to a second staining agent to produce a double-stained specimen. Advantageously, a second staining agent may stain a different cell or tissue component than the first staining agent. Such a second staining agent may be included in a staining composition with the first staining agent or separately, in a second staining composition. The second staining agent may be the same as or different than the first staining agent.

A second staining agent may include a metal stain and/or a non-metal stain producing an electron dense product. Thus, an exemplary second staining agent illustratively includes any of the staining agents set forth hereinabove. Preferred second staining agents include ethidium bromide and/or cis-platinum. In a preferred staining process, the first and second staining agents are different staining agents. Preferably, the use of different staining agents allows for differentiation of components of the specimen. An exemplary staining agent combination includes osmium tetroxide as a first stain, and cis-platinum or ethidium bromide as a second stain to allow for differential staining of cell membranes and nuclei, respectively, so that the staining characteristics of organs and tissues can be further differentiated.

A staining agent may be a cell and/or organelle membrane marker, a nuclear marker, a cytoplasmic marker, a marker for a component of a physiological vascular or interstitial space, and/or a marker for a particular molecule or molecular type.

Stained specimen, with or without a second stain, can be sectioned for true histological sections. For example, osmium-stained cells, tissues and/or embryos may be sectioned for histological examination. Thus, a process disclosed herein is useful as a screen (e.g. a first-line screen) of embryonic defects, from which investigators can perform true paraffin-sectioned histology for the regions identified to be of interest by the methods disclosed herein. The multiple uses of a stained specimen speeds the transition from microCT-based screens to histological verification of suspected morphological phenotypes.

The stained specimen is optionally transferred to one or a series of buffer solutions so as to remove extra staining agents and to create a density contrast between the specimen and its bordering environment t to facilitate distinguishing of the tissue from its bordering environment in images acquired from the tissue. The buffer solutions sodium cacodylate buffer with concentrations in the range of 0.05M to 0.2M, phosphate-buffered saline, and ethanol solutions with concentrations in the range of 20% to 100%.

In a further embodiment, the specimen includes a reporter gene product, and incubating a specimen with the staining agent produces a staining pattern indicative of the presence of the reporter gene product in the stained specimen. Reporter genes, products of genes and agents that interact detectably with the products of reporter genes are generally known in the art. The reporter gene (and its product) may be inherent to the specimen in its wild type or may be introduced into the specimen through chemical or recombinant mutation of one or more components of the specimen. The reporter gene can encode an enzyme, antibody or other functional or structural protein or biologically active agent. An exemplary reporter gene (and its product) is found in a transgenic mammal.

For example, the reporter gene product in a specimen is beta-galactosidase, which is reacted with a staining agent including a substrate for this enzyme, e.g., "S-Gal" (3,4-cyclohexenoesculetin-beta-D-galactopyranoside), and a staining agent, e.g., ferric ammonium citrate, to produce an electron dense product in the specimen. In such an embodiment, the specimen may be first incubated with a staining agent which produces a product indicative of the reporter gene product, e.g., "S-Gal" (3,4-cyclohexenoesculetin-beta-D-galactopyranoside), and a staining agent, e.g., ferric ammonium citrate, and subsequently or simultaneously with a second staining agent and/or a second species. Alternatively, the specimen may first be stained with a first staining agent and then with a second staining agent which produces a product indicative of the reporter gene product.

In an exemplary embodiment, the reporter gene produces a gene product that is an appropriate substrate for automated and/or applications involving color selection. As set forth above, an exemplary reporter gene encodes beta-galactosidase. Insertion of a DNA fragment into a vector multiple cloning region embedded in the alpha-complement of the lacZ gene disrupts beta-galactosidase activity in the host, resulting in diminished beta-galactosidase activity in host cells and a lower level of staining in these cells than would be seen in host cells in which beta-galactosidase activity is essentially normal. As a result, specimens representing recombinants can be distinguished from those containing the parental vector (e.g., wild type).

A specimen included in an inventive process may be a cell, organ, tissue, embryo, animal, or portion of any of these. A specimen may be obtained from any type of organism, and may also be a cultured cell, organ or tissue.

As mentioned above, an inventive process may find use in a variety of clinical and research applications. In a particular embodiment, an inventive process may be used to monitor effects of toxins, drugs and/or treatments on an animal. Thus, in one embodiment, a first specimen is obtained from an individual animal at a first time and a second specimen is obtained from the same animal at a second time. An investigative, therapeutic and/or investigative procedure may be performed subsequent to obtaining the first specimen and prior to obtaining the second specimen. For instance, a drug or toxin is administered to an animal or tissue and changes in a target tissue is subsequently measured by imaging a specimen obtained prior to administration of the drug (or toxin) and a corresponding specimen obtained after such administration.

An exemplary process for imaging a specimen for a change induced by an environmental factor (e.g., drug, toxin) or genotyptic or phenotypic change, includes incubating a first specimen in a staining composition to produce a first stained specimen, scanning the first stained specimen to produce an image of the first stained specimen and comparing the image of the first stained specimen to a reference scan of a second specimen, which is a stained, unstained or differently stained specimen, generally correspondingly histologically, morphologically, genotypically and/or phenotypically with the first stained specimen to produce a difference image between the first and second stained specimens.

In a preferred embodiment, the specimen is an ex vivo embryo. An inventive process is used to phenotype an embryo having a naturally occurring and/or targeted mutation. For example, an inventive process is applied to phenotype a transgenic embryo. Further, an embryo exposed in utero to a particular drug, toxin or other chemical or biological agent may be screened in order to determine any phenotypic effects of such exposure in one embodiment of an inventive process.

A process for screening an embryo for phenotype is described according to the present invention which includes incubating an embryo in a staining composition to produce a stained embryo, scanning the stained embryo to produce an image of the stained embryo and comparing the image of the stained embryo to a reference scan of a stained, unstained or differently stained embryo to produce a difference image.

In an exemplary embodiment, an X-ray computed tomography scanner is used to produce a microCT image of the mutant animal, and comparing the image of the embryo to a reference to determine differences between the images, thereby screening the embryo for phenotype. In particular, one or more whole, intact embryo is imaged. A reference may be an image of an age-matched control embryo. A reference may also be a stage-matched statistically-averaged control image. A control for a mutant animal will typically be an image of a wild-type embryo or a statistically-averaged image of wild-type stage-matched embryos. A control for an embryo exposed to an agent, such as a drug, treatment, chemical and/or biological agent is typically an image of an unexposed embryo or a statistically-averaged image of untreated stage-matched embryos.

A rapid and inexpensive process for obtaining high resolution virtual histology of transgenic mammal (e.g., mouse) embryos is provided in one embodiment. Using a staining composition to differentially stain tissues followed by volumetric x-ray computed tomography to image whole embryos, high quality data is generated. Specimen scans with resolution of 3 microns or better are obtained in less than 12 hours. For example, isometric resolutions of 27 microns or 8 microns are achieved with scan times of 2 hours or 12 hours, respectively, using mid-gestation (E9.5-E12.5) embryos. Embryos at earlier and later stages of gestation may also be used. For instance, E7-E19 embryos are used in microCT processes according to the present invention. This technique represents a significant improvement in resolution, time, and expense for the quantitative, three-dimensional analysis of developmental patterning defects attributed to naturally occurring and transgenic mutations.

MicroCT-based virtual histology matches or exceeds the tissue contrast achieved by more time- and cost intensive magnetic resonance microscopy, while delivering more than 2-fold higher resolution up to 8 microns for microCT, (Jacobs, R. E., et al., Comput Med Imaging Graph 23, 15-24 (1999), or in some cases up to 6 microns. For increased throughput of these types of studies, multiple specimens are optionally scanned simultaneously in the same field of view.

For example, at lower microCT resolutions (27 microns), as many as 120 specimens, e.g., embryos or 10 fetus/newborn mice or rats, or more can be simultaneously scanned in approximately two hours with adequate quality for post-imaging segmentation analysis allowing the recognition of gross and subtle mutant phenotypes. For increased detail of abnormalities suspected on the low-cost 27 micron scans, the same stained specimens can later be scanned at 8 micron resolution for unprecedented detail of organ subcompartments and fine tissue structures.

The computed tomography image of the mutant animal may include an isosurface rendering of the mutant animal so as to examine the exterior of the animal for anatomical or molecular differences compared to normal animals.

In a further embodiment, the computed tomography image of the mutant animal may include a virtual section of the mutant animal.

Large numbers of images and associated data may be generated using micro computed tomography to image specimens and/or whole embryos. Such virtual histology datasets represent a valuable resource for investigating effects of genetic manipulation such as gene disruption or overexpression in vivo. However, generated datasets relating to one mutation or other variable at a particular embryonic stage may have further value when compared to a second mutation or at a second stage. In order to facilitate access and aid in generation of such comparative data, a computer-based process for collecting, storing and retrieving micro computed tomography images and/or image data is provided according to the present invention.

FIG. 1 illustrates an embodiment of an inventive process which includes generating a digital computed tomography image 12, electronically transmitting the image and/or data to a centralized data storage location associated with a computer 14, retrieving the image and/or data from the storage location in response to a request 16 and electronically displaying or transmitting the image and/or data and/or analysis of the image and/or data to a second location in response to the request 18.

A computer tomography image is generated, for example, according to methods described herein. High resolution volumetric computed tomography (CT) of a specimen may be performed using a commercially available scanner, such as an eXplore Locus SP microCT specimen scanner (GE Healthcare, London, Ontario) or the eXplore Locus RS small animal microCT scanner (GE Healthcare, London, Ontario). More rapid volumetric CT scans of specimens may be performed at lower resolution, such as at 27 micron$^3$ isometric voxel resolution, while longer higher resolution scans, such as 8 micron$^3$ isometric voxel resolution, may also be performed, depending on the desired cost, time constraints and resolution required.

Parameters such as current, voltage, and exposure time are adjusted as appropriate and are kept constant for images to be compared. For each scan, a number of evenly spaced views may be averaged. The scans may be filtered, for instance to avoid saturation of the detector, using appropriate filters, such as 0.2 mm aluminum.

Images are reconstructed using appropriate software, such as EVSBeam© software. Preliminary visualizations and virtual histology sections may be generated with the publicly available MicroView© program. Isosurfaces renderings and volume renderings of the CT datasets are generated as images, for instance, as described in Example 1.

A generated computed tomography image and/or data for generating such an image may be stored electronically, in memory circuitry such as a database, and/or on a computer readable storage medium. A generated computed tomography image is communicated to a repository for such images, a centralized image and/or image data storage location associated with a computer. Thus, for example, three-dimensional reconstructions of transgenic and wild-type mouse embryos are generated and images and/or data for image generation is sent to a centralized storage location associated with a computer. Such images and data for image generation may be generated and communicated from multiple locations for centralized storage.

Communication of generated images and/or image data is preferably over a wired or wireless connection to a device or system configured as a server or computer network accessible by multiple users from multiple locations. The server or computer network may include any type of computer device or devices such as a personal computer, workstation or mainframe computer.

Processing and memory circuitry is included in the server or computer network such that an image and/or image data may be communicated to memory circuitry and stored. Further, the stored information may be retrieved from the memory circuitry. Optionally included is a comparison program executable by the circuitry to carry out a comparison of one images or set of images with another set of images in order to characterize differences between the images relating to anatomical and/or molecular differences in specimens imaged. Such a comparison program may be stored and executed on a server or computer network which also includes the stored image and/or image data. A comparison program may also be stored and executed by a separate device to which images and/or image data retrieved from the memory circuitry of the server or computer network are downloaded.

An image and/or data for generating an image may be retrieved from the centralized storage location in response to a request. For example, a user inputs information to a device having data input and output capacity to communicate a request to retrieve an image and/or image data from the server or computer network storage location. The image and/or data may be displayed to the user and/or downloaded to the user's device. Further, the retrieved image and/or data may be retrieved for analysis and results of the analysis displayed or downloaded to the user.

A challenge the small animal research community faces is to combine high resolution anatomical imaging data with highly-sensitive, low resolution molecular (physiological) imaging information. Live animal computed tomography (microCT) offers spatial resolutions as low as 27 μm isometric resolution, but generally this modality does not provide useful information about the physiology of the animal. In contrast, luminescent and fluorescent imaging tracks the migration of cells or to interrogate gene expression and protein function, but is limited by spatial resolution of 1 mm. Although the resolution of small animal positron emission tomography (microPET) is similar to optical methods, microPET benefits from higher sensitivity and greater depth of signal. Small animal magnetic resonance (microMRI) instruments offer anatomical imaging resolution similar to microCT, and are emerging as a technology for intermediate-sensitivity molecular imaging as well. However, no single modality meets the complete needs of studying preclinical mouse models and therefore data from two or more modalities often needs to be combined.

With co-registration of the anatomic and functional image, one can interrogate pathophysiology in an anatomical context for mouse models of human diseases. Simple rigid or statistically-guided co-registration methods overcome the limitations of any single modality and improve qualitative and quantitative information. More recent dual modality instruments combine microPET and microCT, microSPECT and microCT, or microPET and small animal MRI. However, a more common paradigm is that academic medical centers have individual modality instruments at different sites, requiring a method to co-register datasets taken at different times from different instruments.

To facilitate co-registration of anatomical and functional images, a multimodality small animal chamber is designed that can be used with widely available microCT, small animal MRI, microPET and optical imaging instruments. Key features of this chamber include (1) construction with non-metallic material that minimally attenuates x-rays, luminescence, and fluorescence, (2) an accurate system of repositioning animals for serial studies, (3) simple inexpensive fiducial markers, (4) air-tight seals to permit the use of inhaled anesthetics, (5) an in-line micro filter for inhaled and exhaled gases, allowing animals to be scanned irrespective of health/infection status, and (6) rigid foam mouse bed with an attenuation similar to air that makes the holder "invisible" at the image analysis stage.

A specimen holder, e.g., a multi-chamber specimen holder, for use in imaging methods generally, and the imagining method described herein, specifically (e.g., computed tomography) is provided according to the invention. In an exemplary embodiment, there is provides an inventive multi-chamber specimen holder includes multiple chambers, each chamber having a wall defining an internal space for containing a specimen. An inventive holder includes a number of chambers in the range of about 2 to 200. In a preferred embodiment, an inventive holder includes a number of chambers in the range of about 50 to 150. An included specimen chamber includes a side wall and bottom wall, the bottom wall including a support portion for support of a specimen placed in the chamber. In one embodiment, at least the support portion of the wall has a surface which contacts a specimen which is highly transparent to radiation used in an imaging procedure to be performed on the specimen. In a further embodiment, a larger portion of the wall, or the entire wall, is highly transparent to radiation used in an imaging procedure to be performed on the specimen.

Chambers are generally approximately uniform in shape and size. A suitable shape is rectangular, but other shapes may be used.

Chambers in an inventive holder are arranged so that a number of specimens may be imaged in a single imaging field. In one embodiment, chambers are arranged such that the space between them is minimized. For example, at least a portion of the chambers may be configured as a plurality of adjacent laterally arranged chambers. Optionally, at least a portion of the chambers may be configured to share a side wall.

In a further embodiment, an inventive holder may be configured to include more than one plurality of adjacent laterally arranged chambers. The two or more pluralities may be arranged in a layered fashion with respect to each other.

A plurality of adjacent laterally arranged chambers may be configured to share a base. Such a base may be a continuous piece contacting the side walls of the chambers and forming the support portion of the chambers. In such a configuration the plurality of chambers and base form a layer component which may be moved as a single unit. In one embodiment, multiple layer components are included in an inventive holder.

In a preferred option, a receptacle for one or more layer components is provided for supporting and maintaining an arrangement of the one or more layer components during an imaging procedure. In a preferred embodiment, a provided receptacle has a wall formed such that the receptacle is cylindrical or substantially cylindrical in shape and defines an internal volume for containing one or more layer components. One or two end components are optionally provided for further containing the one or more layer components in the internal volume. An end component may be integral to the receptacle, reversibly attached to the receptacle or fixedly attached to the receptacle. Where two end components are provided, at least one of the end components is configured to move such that one or more layer components may be inserted and removed from the receptacle for imaging.

A provided receptacle is preferably configured such that at least a portion of the receptacle present in an imaging field is substantially transparent to radiation used in an imaging process used to image specimens contained therein. The term "substantially transparent" is intended to mean that passage of most of the electromagnetic radiation used to produce an image in an imaging procedure passes through the receptacle unattenuated. In a preferred embodiment, about 85 to 100% of electromagnetic radiation used to obtain an image is not attenuated by the substantially transparent receptacle or a substantially transparent portion thereof. In a further preferred embodiment, about 90% to 100% of electromagnetic radiation used to obtain an image is not attenuated by the substantially transparent receptacle or a substantially transparent portion thereof. In one embodiment, a receptacle includes a receptacle wall present in an imaging field during imaging which is substantially transparent to radiation used in an imaging process.

A material which is used to form a substantially transparent wall or other component for use in a receptacle or other portions of an inventive holder, includes plastics, aerogels and glasses substantially transparent to radiation used in imaging at a desired thickness of the wall or other component. In general, a receptacle wall ranges in thickness between about 0.1 millimeter and 10 centimeters, inclusive. Suitable plastics illustratively include an acrylic resin, a polycarbonate, a polypropylene, a polyurethane resin, a polyethersulfone, or a combination of any of these.

A wall or portion of a wall of a chamber included in a holder according to a preferred embodiment of the present invention is highly transparent to radiation used to image a specimen in the chamber. Thus, a wall or a portion thereof present in an imaging field is preferably highly transparent to radiation used to image a specimen in the chamber. The term "highly transparent" is intended to mean that more than 90% of the radiation passes through the wall or portion of the wall unattenuated. In a preferred embodiment, passage of about 98% to 100% of electromagnetic radiation used to obtain an image is not attenuated by the highly transparent wall or portion thereof. In a further preferred embodiment, at least about 99% of electromagnetic radiation used to obtain an image is not attenuated by the highly transparent wall or a portion thereof. A material which is used to form a highly transparent wall or portion thereof, includes plastics, aerogels and glasses substantially transparent to radiation used in imaging at a desired thickness of the chamber wall. In general, a chamber wall ranges in thickness between about 0.1 millimeter and 1 centimeter, inclusive. A preferred material for forming a chamber wall or portion thereof is a closed cell polyurethane foam such as is commercially available from (U.S. Composites, West Palm Beach, Fla.). A particularly suitable foam for use in forming an inventive multi-chamber holder is a foam having a density of about 2 pounds per cubic foot when cured. A computer-cut (CNC) Styrofoam is an alternative to the molded polyurethane foam.

In one embodiment, a plurality of chambers is formed by a molding process, such as form molding.

Figure 2:
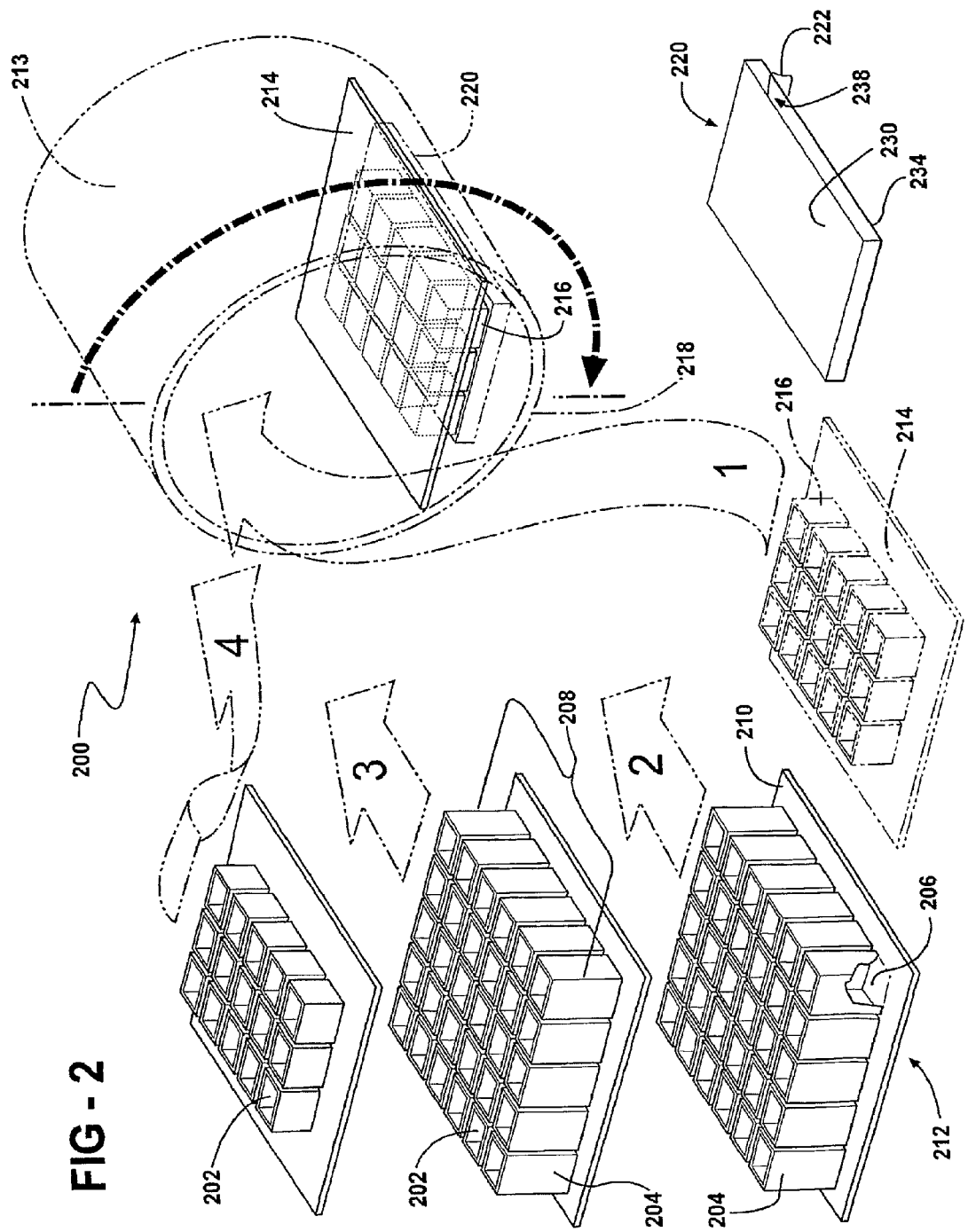
FIG. 2 shows an inventive assembly of a multi-chamber specimen holder.

FIG. 2 shows assembly of a multi-chamber specimen holder 200 in one embodiment of an inventive device. The holder 200 includes multiple chambers 202, each chamber having a wall 204 separating one chamber from another. A support portion 206 of a wall included in the chambers is shown.

FIG. 2 illustrates a plurality 208 of adjacent laterally arranged chambers. A base 210 is shown in association with the plurality 208 of adjacent laterally arranged chambers, defining a layer component 212. In an embodiment illustrated the base 210 also forms a support portion of a chamber wall. Further depicted is an embodiment in which several layer components 212 are included, as well as a receptacle 213 for containing the layer components 212.

An inventive holder, such as shown in a particular embodiment at 200, allows a user to take advantage of the cylindrical internal volume. Thus, in the illustrated embodiment, one layer component 214 is first inserted into the receptacle 213 such that a "top" portion 216 of the wall of the chambers of the layer component 214 is oriented toward the "top" of the receptacle 218. The receptacle is then rotated such that the "top" portion 216 and the "top" of the receptacle wall 218 are positioned downward, such that any specimens in the chambers fall toward the receptacle wall 218. In one such embodiment, the top portion of the chambers 216 is configured to contact the receptacle wall so as to prevent specimens from being disordered. Other layer components 212 may be placed in the receptacle oriented such that specimens are supported by the support portion 206 of the chamber wall during an imaging process.

In an embodiment in which the receptacle wall attenuates radiation used in an imaging process, producing an image of the wall, a liner 220 may be used. A liner 220 may be interposed between the "top" portion 216 of the layer component 214 and the "top" of the receptacle wall 218, so as to separate an image of the specimen from any image of the receptacle wall which might be generated during an imaging process. A liner 220 has a top side 230, a bottom side 234 and a thickness 222 therebetween. Typically, the bottom side 234 is in contact with the "top" of the receptacle wall 218. In a preferred embodiment, at least a portion of top side 230 in contact with a specimen and a portion 238 of the thickness 222 adjacent to the top side 230 are highly transparent to electromagnetic radiation used to obtain an image. This portion 238 has a thickness in the range of about 0.1 millimeter to about 5 centimeters. A holder according to such an embodiment thus allows for generation of the animal image with a reduced or absent adjacent image of the liner, thus avoiding or reducing processing of the image to obtain an isolated image of the animal.

A suitable liner is illustratively a piece of polyurethane foam having a density of about 2 pounds per cubic foot. Such a liner may be formed to fit between the "top" portion 216 of the layer component 214 and the "top" of the receptacle wall 218 and may be further formed to conform to the curve of the curved receptacle wall 218. Other materials may be used to achieve the desired degree of transparency, including plastics, aerogels and glasses which are highly transparent at a desired thickness.

While microCT imaging allows for high resolution imaging of stained specimens and ex vivo embryos, there is a large and developing interest in applications directed to use in imaging live animals as well. For instance, analysis of pre-clinical models for drug safety and efficacy may benefit from use of multiple imaging modes to maximize information gained from a particular experiment. Two or more imaging techniques such as PET, MRI, CT, optical imaging and SPECT, for example, may be used to examine an animal, such that the number of animals used in a study may be reduced.

However, in order to achieve the benefits of multimodal imaging, consistency of animal positioning is important. Further, an animal holder which includes a portion visible in the imaging procedure in close proximity to the image of the animal is undesirable since the holder must be identified and subtracted in subsequent image processing. Thus, in one embodiment, an animal holder for use in imaging is provided according to the present invention which supports an animal and allows for reproducible positioning such that imaging in one or more imaging modes may be performed in a single session and/or at different times. In an additional embodiment, an animal or specimen holder is provided in which at least the surface of the holder which contacts the animal is transparent or nearly transparent to the image-generating signal such that subsequent image processing to remove an image of the holder in close proximity to the image of the animal or specimen is reduced or eliminated.

An animal holder for use in an imaging procedure is provided according to the present invention including a holder body having a wall, the wall defining a support portion for supporting an animal, an internal volume, and an exterior of the device. The wall further includes a passage for moving an animal to be imaged from the exterior of the device to the internal volume of the device.

The wall of an inventive holder is preferably shaped to define an internal volume adequate in size to contain an animal to be imaged. Further, the overall shape of an inventive holder is configured to fit in a gantry of an imaging apparatus. In a preferred embodiment, the overall shape of an inventive holder is configured to fit in a gantry of more than one imaging apparatus such that two or more imaging modalities may be employed.

Figure 5:
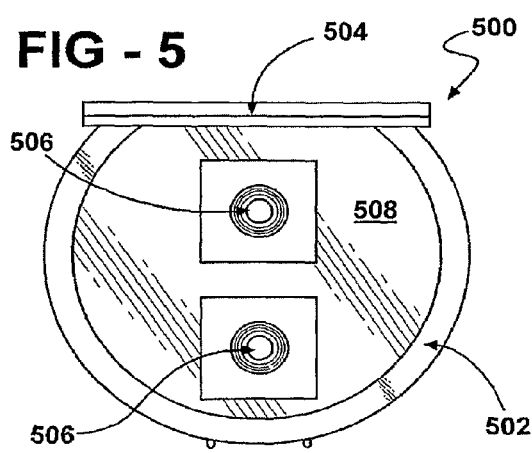
FIG. 5 illustrates a first end-on view of the inventive animal holder of FIG. 3.
Figure 6:
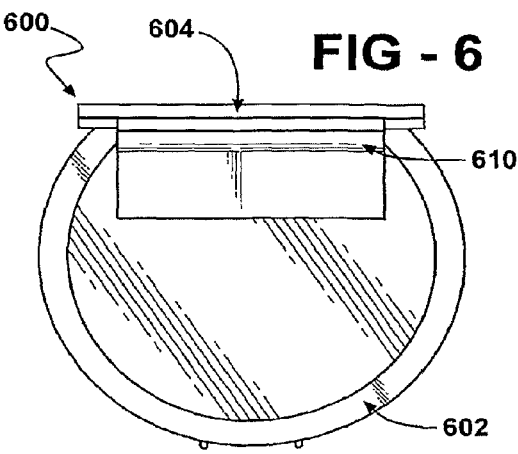
FIG. 6 shows a second end-on view of the inventive animal holder of FIG. 3.
Figure 7:
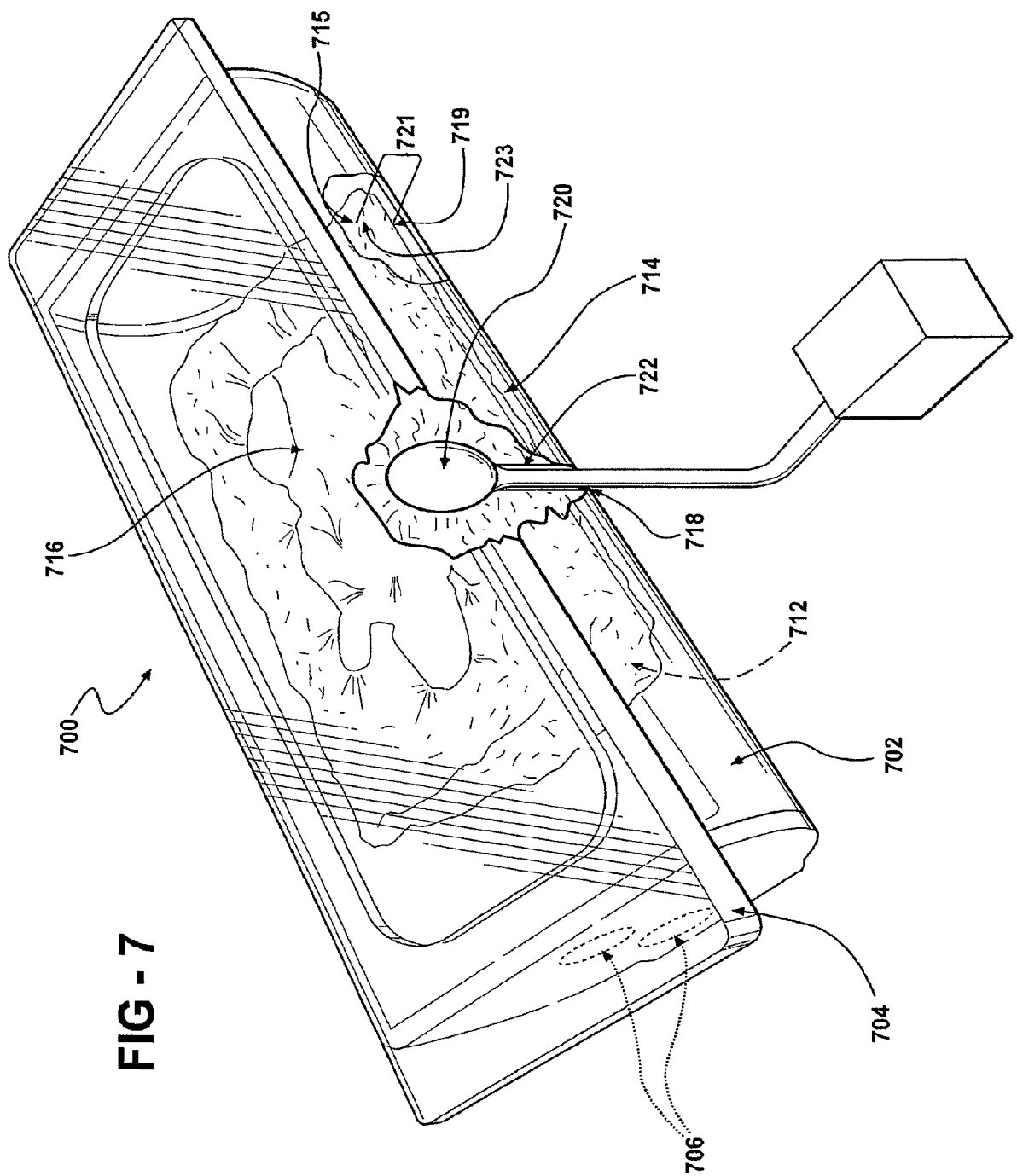
FIG. 7 illustrates an inventive holder including a bed having characteristics optimized for imaging and a port for an animal monitoring instrument.

In one embodiment, an inventive holder has a substantially cylindrical shape to the body. The cylindrical shape may be truncated lengthwise in one embodiment as shown in FIGS. 5-7.

The holder body may be formed of a single wall or of multiple wall components attached to form the wall of the holder.

An inventive device may further include a lid contacting the wall, directly or indirectly, for closing the passage, thereby separating the internal volume from the exterior. The lid is optionally attached to the body. The inventive device may also be used for live animal imaging by maintaining an animal under inhaled anesthesia supplied through two gas ports to avoid any motion artifacts. An additional port may also be used to access the animal to provide optional monitoring, gating, and intubation requirements.

A preferred embodiment includes a substantially flat surface. Such a flat surface aids in optical imaging, such as in luminescence and/or fluorescence imaging. Such a substantially flat surface may be included at any position in an inventive holder relative to a position of an animal. For example, a flat surface is included at the truncated portion of a cylinder truncated lengthwise. An included flat surface advantageously forms a lid to the holder in one option. Such a flat surface is further advantageous in being compatible with an MRI surface coil.

The wall defining the interior volume may also include a gas port defining a passage for one or more gases between the interior volume and the exterior.

Figure 3:
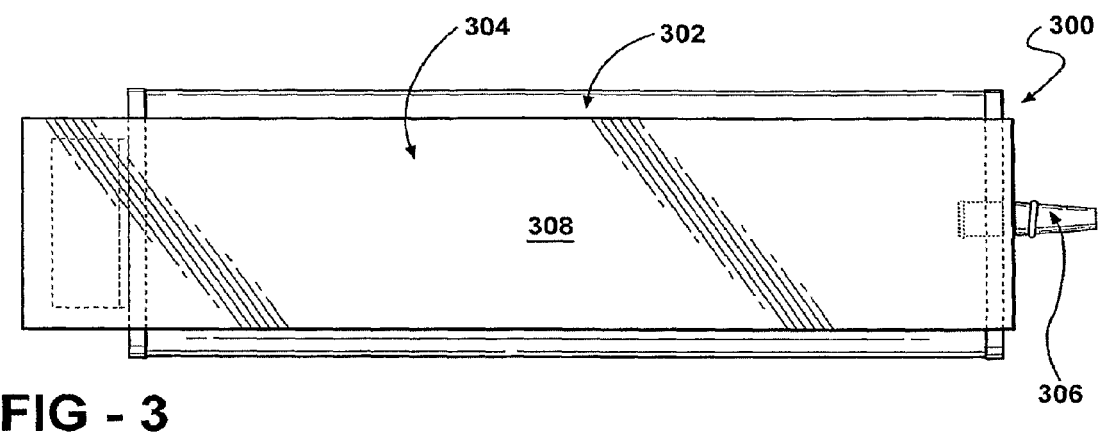
FIG. 3 shows a top view of an inventive animal holder.

FIG. 3 shows a top view of an inventive holder 300 having a wall 302 and a lid 304. In this embodiment, the lid is transparent and the internal volume 308 can be seen through the lid. A gas port is shown at 306.

Figure 4:
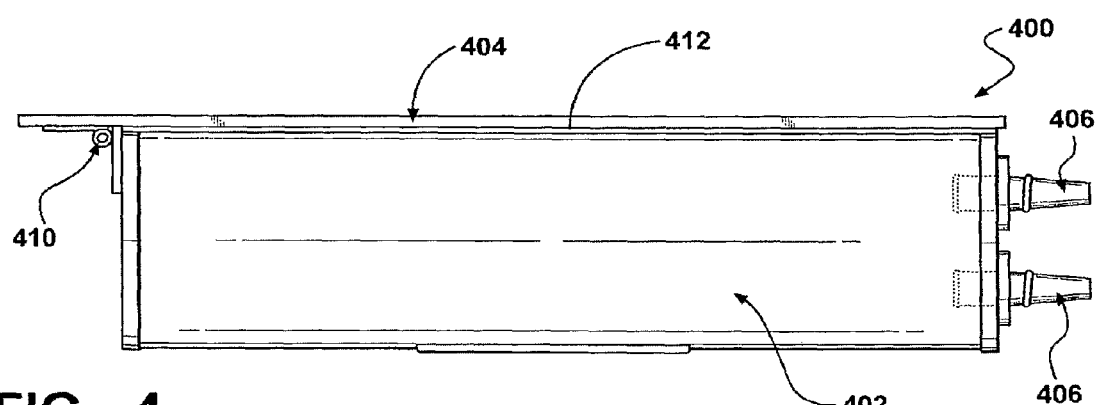
FIG. 4 shows a cut away view of the inventive animal holder of FIG. 3.

FIG. 4 shows a cut away view of an inventive holder 400 showing a body having a wall 402, a lid 404 and two gas ports 406. The lid 404 is shown attached to the body by a hinge 410. A gasket 412 is shown positioned between the wall 402 and the lid 404.

FIG. 5 illustrates a first end-on view of an inventive holder 500 showing a holder body having a wall 502 and a lid 504. Two gas ports 506 are shown which define ports through an end portion 508 of the wall. A wall defining an internal volume of an inventive holder may be a single piece, or may be constructed of multiple attached pieces as is shown in this figure. Here, end portion 508 of the wall is attached to a hollow truncated cylindrical central body defined by wall 502. A second end portion is attached to the wall 502 at the opposing end of the truncated cylindrical central body defined by wall 502.

FIG. 6 shows a second end-on view of an embodiment of an inventive holder 600. Shown is a holder body having a wall 602 and a lid 604. An optional hinge 610 is shown attaching the lid 604 to and end portion of the body wall 608.

A holder according to the present invention includes components, such as the wall and/or lid, constructed so as to include materials that are compatible with one or more imaging modalities such as MRI, CT, PET, SPECT and optical imaging, in order to obtain maximum image quality. In certain embodiments, an inventive holder includes components constructed of material characterized in having limited or no attenuation of x-rays, luminescence, and/or fluorescence. In particular embodiments, non-metallic material is used so as not to interfere with certain imaging modalities, such as MRI.

A preferred embodiment of an inventive holder includes components made of a material which is substantially transparent at a desired thickness to electromagnetic radiation used to obtain an image in one or more imaging modalities. The term "substantially transparent" is intended to mean that passage of most of the electromagnetic radiation used to obtain an image in one or more imaging modalities passes through a component unattenuated. In a preferred embodiment, about 85 to 100% of electromagnetic radiation used to obtain an image in one or more imaging modalities is not attenuated by a substantially transparent component of a holder. In a further preferred embodiment, air-born bacteria or other infectious microorganisms are kept out of an inventive holder where an animal specimen is enclosed for imaging analysis. As a result, degradation of animal tissues or secondary infections associated thereto are reduced and or eliminated. In a further preferred embodiment, about 90 to 100% of electromagnetic radiation used to obtain an image in one or more imaging modalities is not attenuated by a substantially transparent component of a holder. Optionally, three hose barbs, ¼" to 5/16" (VWR International Inc., West Chester, Pa.) are fixed to an end of the chamber, two for inlet/outlet of oxygen and inhaled anesthesis and one for intubation or other monitoring device access.

A material used to form a wall, lid and/or other component which is substantially transparent for use in imaging modalities including MRI, CT, PET, SPECT and optical imaging, includes plastics, aerogels and glasses. In general, a wall or other component ranges in thickness between about 0.1 millimeter and 10 centimeters, inclusive. Suitable plastics illustratively include an acrylic resin, a polycarbonate, a polypropylene, a polyurethane resin, a polyethersulfone, and a combination of any of these.

In a preferred embodiment, a bed for supporting an animal is included in an inventive holder. FIG. 7 illustrates an embodiment of an inventive holder 700 including a body having a wall 702, a lid 704 and an internal volume 708. A bed 712 is shown in the internal volume disposed on a support portion 714 of the wall. The bed 712 includes a portion 716 shaped to conform to the body of a mouse. Gas ports 706 are also shown.

A bed such as illustrated has a top-side 715 having an area 716 which contacts an animal, and a bottom side 719. Typically, the bottom side is in contact with the support portion of the wall 714. In some embodiments, the bed may be in indirect contact with the support portion, such as where an insulating layer or other element is positioned between the support portion of the wall 714 and the bottom side of the bed 719. A thickness 721 extends between the top side 715 and the bottom side 719 of the bed. In a preferred embodiment, at least a portion of the animal contact area 716 of the top side of the bed and the portion 723 of the thickness adjacent to the top side 715 is highly transparent to electromagnetic radiation used to obtain an image in one or more imaging modalities. The term "highly transparent" is intended to mean passage of more than 90% of electromagnetic radiation used to obtain an image in one or more imaging modalities passes through a portion of the animal contact area of the top side of the bed and a portion of the thickness adjacent to the top side unattenuated. In a preferred embodiment, about 98 to 100% of electromagnetic radiation used to obtain an image in one or more imaging modalities is not attenuated by the highly transparent portion. In a further preferred embodiment, at least about 99% of electromagnetic radiation used to obtain an image in one or more imaging modalities is not attenuated by the highly transparent portion. This portion 723 has a thickness in the range of about 0.1 millimeter to about 5 centimeters. This allows for generation of the animal image with a reduced or absent adjacent image of the bed, thus avoiding or reducing processing of the image to obtain an isolated image of the animal.

In one embodiment, the highly transparent portion in the animal contact area and a highly transparent portion of the adjacent bed thickness attenuates electromagnetic radiation used in imaging to an extent similar to air so that image post processing can be performed easily. For example, a closed cell polyurethane foam is a material characterized by attenuation of electromagnetic radiation to an extent similar to air which may be used in the animal contact area of a bed included in an inventive apparatus.

In further embodiments, an accurate system of positioning an animal is included in an inventive holder. In a preferred embodiment, an animal positioning system includes a bed disposed on the support portion of the wall for supporting an animal and maintaining its position. FIG. 7 illustrates an embodiment of an inventive holder in which the bed 712 includes a portion 716 shaped to conform to the body of an animal, such as a mouse. The bed includes a portion shaped to conform to at least a part of the animal to be imaged. In preferred embodiments, the bed conforms to the part of the animal in contact with the bed. For example, the bed conforms to the dorsal part of the animal, including the back, head, limbs and feet, where the animal is placed on its back, or the ventral part of the animal, including the abdomen, chest, head, limbs and feet, where the animal lays ventral side down. Such a bed allows for maximum chest motion over abdominal motion. A bed included in an inventive holder includes a pre-formed portion shaped to conform to at least a portion of an animal to be imaged. For example, a bed may be molded to include a portion having the overall shape of an animal's body. Additionally, the bed is of a material that is disposable and or easily disinfected.

Optionally, a wall included in an inventive holder has a port for a monitoring device or portion thereof, which extends into and/or through the wall to monitor the animal or internal volume of the holder. In a further option, a monitoring device port is included in the bed so that a monitoring device may contact the animal. For example, in a preferred embodiment, an animal respiration monitor is used in order to coordinate optimal image recording conditions with the animal's physical state. For example, a pressure transducer can allow respiratory gating whereby the computed tomography scanner is triggered to take images only during a single phase of the respiratory cycle, minimizing motion artifacts. Thus, an optional feature of an inventive holder is a port for a monitoring device, such as a pressure transducer.

FIG. 7 shows a holder 700 according to the invention having a wall 702 and a port 718 in the wall 702 for an animal monitoring device 720. The illustrated bed 712 further includes a port 722 for an animal monitoring device 720 such that the device may contact an animal positioned in the portion 716 shaped to conform to the body of the animal.

Optionally, at least a portion of the bed surface is pigmented to avoid surface reflection or fluorescence while using an optical imaging system. For instance, at least a portion of the bed is pigmented black or blue to avoid surface reflection.

In a further embodiment, one or more fiducial markers visible with the imaging modalities used in a particular procedure is present in association with an inventive holder to aid in the co-registration process. For example, luminous acrylic (ProArt, Beaverton, Oreg.) is an exemplary material used as a fiducial marker for CT and fluorescence optical imaging. Tritium beads (AmeriGlo, Atlanta, Ga.) are an exemplary material used as a fiducial marker for luminescent optical imaging. Deionized water is an exemplary material used as a fiducial marker for MRI and FDG ([2-18F]2-deoxy-2-fluoro-D-glucose) is an exemplary material used as a fiducial marker for PET imaging. A fiducial marker may be placed on or attached to a component of the holder which will be in the imaging field during animal imaging. For example, a fiducial marker may be attached to the wall of the holder, the lid and/or the bed. Optionally, custom capillary tubes are designed so as to store and deliver these solutions in volumes that are desired. The concentration of the fiducial markers is adjusted to reduce and avoid interferences of its signal with images.

In a preferred embodiment, an inventive holder includes a gas control adapted to control to exchange of air or other materials between the internal volume of the holder and the environment outside the holder in order to help perform studies without contamination of the animal or an imaging facility. For example, seals may be used, particularly at joints and in association with movable parts to inhibit gas exchange and control the environment inside the holder. FIG. 5 shows an exemplary gasket at 512. Such control of gas flow permits the use of inhaled anesthetics introduced into the holder, through a gas port for example.

Gases exchanged through one or more gas ports may be purified, such as by HEPA filtering of inhaled and exhaled gases to permit animals to be imaged irrespective of health/infection status.

Thus a gas control system illustratively includes a component selected from the group consisting of: a closable port in the wall defining a passage for a gas, a gasket, a filter, a gas pump, an anesthesia delivery device, or a combination thereof.

Embodiments of inventive compositions and methods are illustrated in the following examples. These examples are provided for illustrative purposes and are not considered limitations on the scope of inventive compositions and methods.

EXAMPLES

Example 1

Staining methods for use in producing a microCT image according to the present invention are compared with conventional histological sectioning and staining using mouse embryos.

Specimen Preparation

Pax3:Fkhr transgenic mice (Keller, C., et al., Genes Dev 18, 2608-13, 2004; Keller, C. et al., Genes Dev 18, 2614-26, 2004), as well as wild-type mice are used in an example of an inventive process. Embryos are harvested at E9.5-E12.5 gestational ages, then fixed in 10% buffered formalin overnight at 4° C. Hematoxylin and eosin stained paraffin sections are prepared using established methods (Keller, C., et al., Genes Dev 18, 2608-13, 2004), then visualized at 2× magnification on a Nikon Eclipse 80i microscope. Immunohistochemistry with the Pax7 monoclonal antibody (Developmental Hybridoma Studies Bank, Iowa City, Iowa) is performed as previously described (Keller, C., et al., Ibid). For microCT-based virtual histology embryos are then stained according to an inventive process. Embryos are stained to saturation overnight in a solution of 0.1 M sodium cacodylate (pH 7.2), 1% glutaraldehyde, and 1% osmium tetroxide rocking at room temperature. Embryos are then washed for 30 minutes in 0.1M sodium cacodylate buffer, and twice more for 30 minutes in phosphate-buffered saline. Specimens are incubated in a graded series of ethanol concentrations to 100% ethanol prior to scanning.

Imaging

High resolution volumetric computed tomography (CT) of embryos is performed at 8 micron$^3$ isometric voxel resolution using an eXplore Locus SP microCT specimen scanner (GE Healthcare, London, Ontario). This volumetric scanner employs a 3500×1750 CCD detector for Feldkamp cone-beam reconstruction and is similar in performance to other commercially available in vitro scanners under $300,000 that are commonly operated as regional core facilities (virtualhistology.com). In this study, the platform-independent parameters of current, voltage, and exposure time are kept constant at 100 .mu.A, 80 kVP, and 4000 ms, respectively. For each scan, 900 evenly spaced views are averaged from 8 frames/view, filtered by 0.2 mm aluminum. At 8 micron resolution, the field of view of this instrument is 15×15×15 mm. Each scan took approximately 12 hours. Cost of this method is approximate $40 per hour ($480 per scan). Images are reconstructed with the manufacturer's proprietary EVSBeam© software. More rapid volumetric CT scans of embryos performed at 27 micron$^3$ isometric voxel resolution using an eXplore Locus RS small animal microCT scanner (GE Healthcare, London, Ontario). Like the specimen scanner, this live animal volumetric scanner employs a 3500×1750 CCD detector for Feldkamp cone-beam reconstruction and is similar in performance to other commercially-available in vivo scanners under $300,000 that are commonly operated as regional core facilities (ccri.uthscsa.edu). In this study, the platform-independent parameters of current, voltage, and exposure time are kept constant at 450 mA, 80 kVP, and 2000 ms, respectively. For each scan, 450 evenly spaced views averaged from 6 frames/view. At 8 micron resolution, the field of view of this instrument is 45×45×45 mm. Each scan took 2 hours and 4 minutes. Cost of this method is also approximately $40 per hour ($80 per scan). Images are reconstructed with the manufacturer's proprietary EVSBeam© software. Preliminary visualizations and virtual histology sections are generated with the publicly available MicroView© program (microview.sf.net).

Isosurface Generation

Isosurfaces renderings of the CT datasets are generated using a combination of the open-source Teem utilities (Kindlmann, G. Teem. 1.8.0 edn, SourceForge.net, 2005). and the open-source, platform-independent BioImage rendering program ((SCI), S.C.a.I.I. BioPSE: Problem Solving Environment for modeling, simulation, image processing, and visualization for biomedical computing applications., 2002). Both sets of software are available on-line (software.sci.utah.edu). Sub-sampling of the microCT volumes, which are significantly larger than the available memory on current graphics cards, is also performed using the Teem libraries. The final sub-specimen volumes are 255×255×255 and equally spaced using a nearest neighbor approach. Pre-computing of the gradient and Hessian data is also performed using the Teem libraries. The combined process of sub-sampling and generation of gradient and Hessian data produced two data volumes, which are stored together with the original CT values in a "VGH" volume (Value, Gradient, Hessian). The VGH volumes are subsequently used to create isosurfaces in real time with the BioImage software package. Segmentation Image volume segmentations are done using a Watershed algorithm (Mangan, A. P. & Whitaker, R. T., IEEE Trans. Vis. Comput. Graph 5, 308-321, 1999) provided in the National Library of Medicine's Insight Toolkit (ITK, itk.org). Watershed segmentation is a region growing algorithm in which user defined seed points are positioned in areas of interest, and a statistical analysis is made of the gradient magnitude in the local neighborhood to find the standard deviation. The structure is then found as the perimeter of the seed points extend through the continuous surrounding area, without crossing points where the gradient magnitude is beyond one standard deviation of the mean. The resulting structures are saved to disk as separate volumes. Segmentations are done on a computer equipped with 2.5 GHz Intel PENTIUM™ III processor and 2 GB of RAM. The resulting volumes are then combined into one volume by marking each segmentation as a unique value, and then merging it into the original again, such that where the segmentation exists overwrite its original value with the new marked value.

Volume Renderings

The volume renderings of wild type and Pax3:Fkhr mutant embryo data sets are created using direct volume rendering techniques using the in-house software package, Nenners (Johnson, T. N. (2005) Nenners. Nenners reads a volume and casts geometric rays through the volume. The geometric rays are cast from every pixel and sampled twice between voxels, thus x/2 or less where x is the units in which the specimen is scanned. Specimens are acquired by convolution using separable kernels (Gonzalez, R. C. & Woods, R. C. Digital Image Processing. 197, 2002). Cubic B-splines are used to interpolate both the CT value and gradient (Kindlmann, G. L., Whitaker, R., Tasdizen, T. & Möller, T. Curvature-Based Transfer Functions for Direct Volume Rendering: Methods and Applications. Proceedings IEEE Visualization, 513-520, 2003). Color and opacity are defined at each specimen point using a 2-dimensional transfer function, gradient magnitude and x-ray density defining the domain (Levoy, M., Display of Surfaces from Volume Data. IEEE Computer Graphics & Applications 8, 29-37, 1988; Kniss, J. M., Kindlmann, G. L. & Hansen, C. D. The Visualization Handbook., eds. Hansen, C. D. & Johnson, C. R., 189-210, Elsevier, 2005). This is done in a front to back fashion, such that when the opacity of a ray becomes equal to or greater than 1 the ray is terminated early and the next ray is computed. Bounding volumes are also used to speed this process such that rays that have not yet or will not hit the volume are not sampled. The gradient is also used to approximate the Phong shading models used (Gooch, A., et al., A Non-Photorealistic Lighting Model For Automatic Technical Illustration. in Proceedings of ACM Siggraph 447-452, 1998). A curvature based transfer function (Gooch, A., et al., ibid). and depth queuing may also be applied to the volume renderings. The transfer function is based on the dot product of the angle of an incident ray with the surface normal. If the dot product is less than some constant k, 0<k<1, then the surface is marked black to emphasize surfaces perpendicular to the viewing direction. Furthermore, a depth queue, to shade interpolated, specimens is used to give a greater feeling of depth and separate foreground from background. Parameters of camera position, viewing direction, and lighting, relative to the specimen are also passed to define the view of the rendering. The software is run on an SGI Onyx 3800 at 80 seconds per rendering, each row of pixels can be distributed over hyperthreaded or multiple processors for faster results.

Using the above-described processes, formalin-fixed wild-type E11.5 embryos whose cell membranes are stained in a 1% solution of osmium tetroxide are imaged by volumetric computed tomography at 8 micron isometric resolution. External surface features of the scanned embryos may be represented as isosurfaces, demonstrating a level of detail comparable to a dissection microscope. Internal structures are visualized by a semi-transparent Maximum Intensity Projection (MIP) of the entire embryo.

In order to compare the spatial resolution of traditional optical histology to microCT-based virtual histology, paraffin-embedded 4.5 micron sections are stained with hematoxylin and eosin and visualized at 2× magnification. Sagittal, coronal, and axial sections by microCT-based virtual histology are comparable in the delineation of internal features (organs and tissues) to paraffin-sections at the same magnification. Anatomical landmarks as small as the dorsal root ganglia, the neural tube, and the anterior cardinal vein could be easily discerned. Because osmium staining increases with lipid content of tissues, a six-fold difference in densities is observed in this example from the least stained tissue to the best stained tissue. CT density values of tissue ranged from 5785 to 32767 Hounsfield units.

Example 2

Whole embryos at gestational ages with limited epidermal layers are used in particular examples of inventive processes. For instance, midgestation whole embryos (E8-E13.5) that lack significant epidermal development may be used, and skinned embryos up to E19 can be satisfactorily stained as well. Embryos as stained as described in Example 1. Isosurfaces and sagittal crossections of a time series of E9.5, E10.5, E11.5, and E12.5 embryos are performed, scanned at 8 micron isometric resolution. At these resolutions, features such as the developing brain vesicles, neural tube, heart chambers, and liver can be clearly delineated. Due to the increased lipid content of the liver, attenuation of osmium-stained hepatic tissue results in the highest opacity and brightness.

Example 3

Rapid 27 Micron Resolution Scans.

A GE eXplore RS small animal scanner is used to perform scans of wild-type E12.5 embryos at 27 micron isometric resolution in approximately two hours. The embryos are stained as described in Example 1. A comparison of 8 micron and 27 micron scans of the same embryo shows that while 8 micron sections display considerably higher spatial resolution, the 27 micron sections are nonetheless adequate to distinguish features such as the semicircular canal, the neural tube central canal, and the cardiac chambers. From the perspective of high throughput phenotyping, the resolution of these 27 micron microCT scans are in the range of magnetic resonance microscopy, but at a nearly six-fold time savings. Furthermore, these 2 hour, 27 micron resolution scans are adequate to perform high quality segmentation analysis of major organ compartments, an advantage for computer-based, automated phenotyping. A caveat is that the small lumens within some organs, such as the right atrium of the heart, is less well segmented than the higher resolution scan. However, the same osmium-stained embryo scanned at 27 micron resolution can be scanned at 8 micron resolution when increased definition of smaller structures is necessary.

Example 4

To test the value of microCT virtual histology for high throughput phenotyping for major organ compartments and tissue structures of younger embryos, Pax3:Fkhr transgenic mouse embryos are utilized which are known to have complex rostral neural tube malformations (Keller, C., et al., Genes Dev 18, 2608-13, 2004, Keller, C. et al., Genes Dev 18, 2614-26, 2004). These embryos express the Pax3:Fkhr fusion oncogene in place of the Pax3 gene in the dorsal neural tube and the dermomyotome, resulting in partial failure of neural tube closure. Wild type and Pax3:Fkhr mutant E11.5 embryos are stained as in Example 1 and scanned at 27 micron resolution, then renderings with segmentation are performed to visualize the cephalic forebrain, midbrain, and hindbrain vesicles, the heart wall and cardiac ventricles, and the liver. With these renderings one can appreciate failure of neural tube closure at the level of the hindbrain and midbrain, overgrowth of the midbrain mesenchyme, as well as the hypotrophy of the telencephalic vesicles. While these findings would have been apparent with real histology derived from paraffin-embedded specimens, the complex global three-dimensional organization of the mutant forebrain, midbrain, and hindbrain would not have been. The cardiac ventricular wall is essentially the same between wild type and mutant at this age, with no appreciable difference in the volume or patterning of the common ventricle. The liver also appears to be patterned normally in both wild type and the mutant. Using individual 27 micron planes, an additional subtle defect is detected in the neural tube at the level of the hindlimbs in association with severe blunting and disorganization of the dorsal neural tube. From the point of view of a semi- or fully-automated high throughput screen for developmental patterning defects, the rapid 27 micron scan represents a feasible method of morphological typing of both complex gross and subtle features.

Example 5

Staining methods for use in micro CT-scanning are compared using mouse embryos.

Embryo Harvests: Embryos are harvested at the 12th day of gestation (E12.5), then fixed in 10% buffered formalin overnight at 4° C.

A first staining method is performed in which embryos are stained in a solution of 0.1 M phosphate buffer (pH 7.2) with 2% osmium tetroxide rocking at room temperature for 1 hour. Embryos are then washed for 30 minutes in 0.1M phosphate buffer, and twice more for 30 minutes in phosphate-buffered saline. Specimens are then transitioned by a series of gradients to 100% ethanol prior to scanning.

A preferred staining method according to the present invention is compared with the above described "first staining method." In an inventive method, embryos are stained to saturation overnight in a solution of 0.1 M sodium cacodylate (pH 7.2), 1% glutaraldehyde, and 1% osmium tetroxide rocking at room temperature. Embryos are then washed for 30 minutes in 0.1M sodium cacodylate buffer, and twice more for 30 minutes in phosphate-buffered saline. Specimens are then transitioned by a series of gradients to 100% ethanol prior to scanning.

The same scanning methods are used to compare specimens processed by the first method and by the described inventive method. E12.5 embryos stained by the two different methods are placed in the same tube and scanned together at the same time. CT scans of embryos performed at 27 micron$^3$ isometric voxel resolution using an eXplore Locus RS small animal microCT scanner (GE Healthcare, London, Ontario). This live animal volumetric scanner employs a 3500×1750 CCD detector for Feldkamp cone-beam reconstruction and is similar in performance to other commercially-available in vivo scanners under $300,000 that are commonly operated as regional core facilities. In this study, the platform-independent parameters of current, voltage, and exposure time are kept constant at 450 mA, 80 kVP, and 2000 ms, respectively. For each scan, 450 evenly spaced views averaged from 6 frames/view. The scan took approximately 2 hours and 4 minutes. Three dimensional volumes are reconstructed with the manufacturer's proprietary EVSBeam© software. Visualizations are generated with the manufacturer's MicroView© program.

Results of this study show background noise due to ethanol which overlaps with the signal range of material processed by the "first method." In contrast, the signal range of tissue processed by the above-described inventive method is well isolated from the background noise range due to ethanol. Further, tissue stained according to an inventive method generates a signal having a wider range of "Ct values" compared to tissue stained according to the described "first method." Thus, an image generated using an inventive process shows a larger range of signal intensities and a better signal to noise ratio than an image generated by the described "first method."

Example 6

Fetuses are dissected in cold PBS after first cutting the umbilical cord cleanly with a scalpel (not with scissors or by tearing; this is important to optimize vessel imaging). Both the amnion and the inner thin serosa membrane (have as little extra-embryonic/extra-fetal tissue as possible) are then carefully removed. The cleaned fetuses are placed in PBS on ice. For fetuses coming out of transgenic animals, a small (1.5× 1.5 mm) piece of the amnion or inner membrane is placed in a 1.5 ml tube. The tube is labeled with unique identifier number for the animal. A photograph of the fetus is taken under a dissecting microscopy. All embryos/fetuses are individually labeled by a unique identifier number. Each fetus is stored in a pre-labeled glass screw-lock tube that has been previously acid-treated with 0.1N HCl followed by copious ddH$_2$O wash. For fetuses/pups, skin should be removed before fixing and staining. To loosen the skin for easy skin removal, blanch before skinning. To do so, a small beaker is filled with water and the water is brought to a boil on the hotplate; while the water is to be boiled, a small, a shallow "X" on the ventral and dorsal sides of a mouse fetus/pup is cut using a micro-scissor. FIG. 8 shows the morphological changes of a fetus just after being freshly euthanized (A), then after being blanched (B), and then after being skinned (C) in accordance with the description above.

Example 7

After the steps of blanching and skinning, incisions on the fetuses are made to open their thoracic pleura, abdominal peritoneum, and dura matter to further enhance stain penetration.

To open the thoracic pleura, a short supracostal incision is made with a scalpel above the tenth rib on the left lateral side of the body, as shown in FIG. 9A. Since nerves and vessels run below each rib, making the incision above the rib will less likely cause damage to a vessel which can lead to unwanted hemorrhages. Additionally, since the tenth rib is located anterior-lateral to the gap between the lungs and the diaphragm, making the incision above the tenth rib is less likely cause damage to the internal structures. Delicate scissors are then used with the tips up to extend the cut along the top edge of the tenth rib to approximately 2 to 4 mm in length without damaging any internal structures such as the lungs and the heart. The supracostal incision/cut for the right lateral side of the body is then repeated as shown in FIG. 9B. The cut is no deeper than 1 mm from the surface so as to open only the thoracic pleura and not damage any internal organs.

Likewise, to open the peritoneum, a small vertical incision is made with a scalpel along the midline of the abdominal cavity 1 mm above the umbilicus, then delicate scissors are used with the tips up to extend the cut to approximately 1.3 mm in length in the direction of the xiphoid process cutting only the abdominal peritoneum without damaging any internal organs, as shown in FIG. 9C. Making the incision less than 1.3 mm in length ensures the cut to be inferior to the liver thereby having less of a chance of damaging the liver. The cut is no deeper than 0.3 mm from the surface to prevent damage to the intestines.

To open the dura mater, a 2 to 3 mm long incision is made with a scalpel along the suture of the skull as shown in FIG. 9D. It is noted that the cut should be no deeper than 0.5 mm from the surface. So as to open only the dura mater but not to damage other structures in the brain.

After the incisions, each fetus is transferred to a 50 ml conical tube and washed by rocking with PBS for 2 to 10 minutes three times before fixing to remove all extraneous membrane and tissue bits so as to prevent any artifacts. The fetus is incubated in either 10% buffered formalin or Fix Solution rocking overnight at room temperature with a fixative volume about ten times the volume of the fetus itself. The Fix Solution contains 0.1M cacodylate buffer and 1 to 3% by weight glutaraldehyde. An overnight (12 hour) fixation at room temperature for fetuses is a minimum. Such well-fixed fetuses are stored 6 months without adversely affecting the subsequent staining methods.

Example 8

A method is provided below for preparing and fixing non-embryo tissues such as liver, heart, lung, etc.

A glass vial is acid-treated with 0.1N HCl followed by copious ddH$_2$O rinse. A tissue is measured and cut and placed in the treated glass vial. The tissue is then incubated in either 10% buffered formalin or the Fix Solution rocking overnight at room temperature. The fixative volume is preferred to be ten times the volume of the tissue itself.

After the fixation, the fixation fluid is removed from the tissue. The tissue is then stained with 0.8 to 2% OsO4 staining solution also containing 0.1M cacodylate buffer and 1% by weight glutaraldehyde. For thin tissue sections <2 mm, 1% OsO$_4$ staining solution in 4 ml acid washed glass vial is used; for thick tissue sections >2 mm, 1.84% OsO$_4$ staining solution in 4 ml acid washed glass vial is used. The tissue section is incubated at 4° C. for 6 to 12 hours by rocking. This staining and incubation step may be repeated with a fresh preparation of OsO$_4$ staining solution.

It is noted that osmium tetroxide and its solutions should be stored without exposure to light, heat, or organic materials to prevent the formation of osmium dioxide, a black compound that is ineffective for fixation purposes.

Example 9

A method is demonstrated below for staining tissues with phosphotungstic acid (PTA).

Tissues are fixed overnight in 10% buffered formalin by rocking at room temperature. The tissues are rinsed in 1×PBS three times for 1 hour each rinse. The tissues are then stained overnight in 5% phosphotungstic acid (Electron Microscopy Sciences) by rocking at room temperature. The tissues are again rinsed in 1×PBS three times by rocking for 1 hour each rinse. The tissues are then dehydrated in graded ethanols, specifically in 25% ethanol in 1×PBS by rocking for 15 to 30 minutes; 50% ethanol in 1×PBS by rocking for 15 to 30 minutes; 75% ethanol in 1×PBS by rocking for 15 to 30 minutes; 100% ethanol in 1×PBS by rocking for 15 to 30 minutes; and another 100% ethanol in 1×PBS by rocking for 15 to 30 minutes. After dehydration, the tissues are packed in a loose sponge in 100% ethanol in a micro-centrifuge tube and ready for scanning.

Example 10

In one example, an inventive holder body is constructed of a 3" OD cylinder made of plexiglas having a 3 mm wall thickness (Plastic Supply of San Antonio Inc, San Antonio, Tex.). The cylindrical design in this embodiment maximizes the space available in the gantry of many CT/MRI/PET machines. The top surface of the cylinder is cut 1 cm from the outer surface in order to provide contact points for a lid for the holder. A lid is made from 3 mm thick flat cell cast Acrylite® FF sheet (Atoglas, Philadelphia, Pa.). This sheet is optically clear and is considered to have 90% visible light transmission. Two holes are cut in one end of the cylinder wall and two hose barbs, ¼" to 5/16" (Plastic Supply of San Antonio Inc, San Antonio, Tex.) in the holes for inlet and outlet of oxygen/isoflurane enabling respiratory anesthesia and/or air exchange. The junction between the holder lid and holder body is precisely machined to make the injunction air-tight. Optionally, this process may further employ the use of a closed cell sponge rubber gasket (Rubber Cal, Santa Ana, Calif.) placed in contact with both the holder lid and holder body at the junction. The lid is fixed to the body with clear plastic hinges and clasps (Tap plastics, Santa Rosa, Calif.).

Example 11

A luminescence and fluorescence transmission test of a holder according to the present invention including an ACRYLITE™ FF lid is performed on a XENOGEN™ IVIS-200 instrument. A 10 micromolar solution of FITC and Cy 5.5 are used to check the transmission of fluorescence, and tritium gun sight material is used to check for transmission of luminescence. To check the effect of signal attenuation within the tissue, a tritium source is placed inside mouse abdomen and the signal is recorded with and without the ACRYLITE™ FF lid. The results show a 93% transmission with the holder lid. Minimal attenuation of optical signal by the holder lid surface is observed. Fluorescence and luminescence transmission tests are performed with and without lid using solutions or in animals. FITC has a transmission through the holder of 89%. Cy 5.5 also has a transmission through the holder of 89%. Tritium luminescence has a higher transmission through the holder of 92%. Tritium inside mouse abdomen has a transmission through the holder of 93%.

Example 12

A tritium source is placed inside the mouse abdomen and the luminescent image is registered. The fiduciaries are also luminescent so as to be visible in the intensity map generated in this example. The mouse is scanned in the microCT and its 2D Maximum Intensity Projection (MIP) image is used for co-registration. The fiduciaries are used as reference markers to overlap the images. It is seen clearly from the overlapped image the activity of tritium corresponds to the anatomic location in the CT image.

Successful coregistration of microCT and luminescent optical imaging datasets is achieved using an animal holder according to the present invention. Coregistration results from microCT/Optical and microPET/MRI show good correlation between the two registered images. In these tests, a mouse is anesthetized using isoflurane and a tritium source is placed inside its abdomen. The animal is positioned inside an inventive holder on a customized foam bed which includes several fiducial markers. The fiduciary is brought down to desired concentration by dilution with double-distilled $H_2O$ to avoid any lead particle contamination. The holder lid made of Acrylite FF is sealed against the body of the holder using rubber gaskets to inhibit gas exchange at the junction of the lid and holder body. A luminescent image is acquired with 4 sec exposure time, highest resolution, 12.7 cm field of view, f/stop of $\frac{2}{8}$, and 3 cm specimen height. Subsequently, the holder is transferred to a microCT instrument and a CT image is acquired with 93 micron resolution, 4 frames to average, 720 views, 100 ms exposure time, 80 kVp X-ray source power, and 450 uA source current within 25 minutes. The image is corrected and reconstructed to get a 3D image with slices in the axial, sagittal and coronal planes. A 2D MIP image is generated to be used for co-registration using Microview. The images from the modalities are fused together using Power Point. The height of the tritium source inside the abdomen is measured from both the modalities, giving a measurement from an axial view in CT of 5.15±0.5 mm and giving a measurement from 3D reconstruction in optical imaging of 5.00±0.5 mm.

In further examples, an inventive holder is used for successful coregistration of small animal MR and microPET datasets.

MicroCT Imaging parameters used in this example are described herein. All animals used for this study are treated in accordance with an IACUC approved protocol. Mice are anesthetized using 1% isoflurane in 100% oxygen at 2.5 liters per minute flow. Luminous acrylic (ProArt, Beaverton, Oreg.) is used as a fiducial marker and is visible in optical/PET imaging due to its luminous property and in CT/MRI due to its acrylic properties. The concentration of the liquid is brought down to the desired level so that it does not affect the actual signal from the mouse and is placed in single strip tubes at three locations around the specimen. Volumetric computed tomography (CT) of anesthetized mice is performed at 93 $um^3$ voxel resolution using an eXplore Locus RS Small Animal microCT Scanner (GE Healthcare, London, Ontario). This volumetric scanner employs a 3500×1750 CCD detector for Feldkamp cone-beam reconstruction and is similar in design to other commercially-available in vivo scanners under $300,000 that are commonly operated as regional core facilities (ccri.uthscsa.edu). In this study, the platform-independent parameters of current, voltage, and exposure time are kept constant at 450 uA, 80 kVP, and 100 ms, respectively. Scan parameters included 720 evenly-spaced view angles and four frames are averaged per view. Images are reconstructed with the manufacturer's proprietary EVSBeam© software, and visualizations are generated with the open-source MicroView© program.

Luminescent and fluorescent imaging in this example is performed using XENOGEN™ IVIS 200 system (Xenogen Corp., Alameda, Calif.). This imager employs a scientific grade, cryogenically cooled CCD camera which has a low noise 16 bit digitized electronic readout. In this study, the parameters used are 4 sec exposure time, highest resolution binning, 12.6 cm field of view, and f/stop of 2/4. the data is acquired using the manufacturer's proprietary Living Image 2.5 © software and 3D images are reconstructed using Living Image 3D © software.

Example 13

A successful co-registration of microCT and luminescent optical imaging datasets is demonstrated below.

To demonstrate the effective use of the chamber for co-registration of microCT and optical imaging, two sets of scans are performed. For microCT/Luminescence, an animal with a luciferase reporter gene expressed from the right thigh is used. The animal expressing luciferase is induced with anesthesia using isoflurane, injected with luciferin and positioned in the customized foam bed. Three fiducial markers (short capillary tubes) are placed along side the mouse in the foam bed, which is then placed inside the multimodality chamber. Optical and a microCT image acquisition, reconstruction and coregistration are performed as detailed above. From the co-registered image as shown in FIG. 10A, one can appreciate the signal localization in the right thigh of the animal. Total signal intensity was 1.38×107 p/s.

Example 14

Another successful co-registration of microCT and luminescent optical imaging datasets is demonstrated below.

To demonstrate the effective use of the chamber for co-registration of microCT and optical imaging, two sets of scans are performed. For microCT/near-infrared fluorescence, a tumor bearing animal that had been administered a tumor-selective near-infrared contrast agent is used. Similarly, the mouse with a spontaneous leiomyoma in the uterus is imaged after tail-vein injection of a modified Indocyanine Green contrast agent. Near-infrared imaging is performed 15 minutes after injection. The signal from the tumor region is quantified to be $4.149 \times 10^{10}$ pulses/second. The animal is then transferred to the microCT to perform a 93 cubic micron scan. The Optical (2D) data is co-registered to microCT (3D) data with the help of fiducial markers as shown in FIG. 10B. The animal is then necropsied (inset). From the co-registered datasets one can appreciate that the signal has clear boundaries, with most of the signal concentrates in the viable, solid tumor region. These two datasets demonstrate the compatibility of the chamber with CT and optical systems, and the ease with which datasets from two modalities can be co-registered.

Example 15

A successful co-registration of small animal MR and MicroPET datasets is shown below.

To demonstrate the feasibility of usage with MRI and PET systems, a healthy, wild type mouse is imaged to co-localize anatomy and normal glucose metabolism. The mouse is positioned over the foam bed along with its fiducial markers and placed inside the multimodality chamber. A 3-D MRI image is acquired with a 0.38 mm isotropic voxel resolution and total acquisition time of 20 minutes. Immediately after the MRI imaging session the mouse is transported to the microPET scanner in an adjacent room. An intraperitoneal injection (i.p.) of 0.25 mCi $^{18}$F FDG is administered to the animal which is then placed back into the chamber. The customized foam bed allows the mouse to be reproducibly positioned after i.p. injection. After allowing a 15 minute blood circulation time, a microPET image sequence is acquired over 25 minutes. A 3D reconstruction of the microPET image shows glucose metabolism activity in the central nervous system of the mouse. The data is co-registered with the 3D maximum intensity projection image generated by the microMRI as shown in FIGS. 10C, D, E. The coregistered data helps one to appreciate the anatomical localization of glucose metabolism in the myocardium, central nervous system, and salivary glands with the strongest signal from the olfactory bulbs.

This data demonstrates the compatibility of the chamber with microMRI and microPET systems and the reproducibility of positioning in the foam bed.

Example 16

An exemplary protocol to make the foam mold bed used as a positioning system is detailed. A foam bed is molded from urethane foam (U.S. Composites, West Palm Beach, Fla.) which is a two part, pour in place liquid that when combined will expand into a rigid, closed cell polyurethane foam. The foam used here is 1.8 to 8 pound per cubic foot density which has a density similar to air.

The two parts of the foam are first measured and mixed together in a plastic container. The liquids are mixed vigorously for 25 seconds and then transferred into the special plastic mold having an impression of a mouse body therein. Several plastic molds are made having three different sizes to accommodate small, medium and large mice. The plastic mold is also covered with a commercial available mold release wax (U.S. Composites, West Palm Beach, Fla.), that helps for easy release of the foam and avoids any damage to the plastic mold. Within a 45 seconds period the foaming process begins and the foam will fully expand in 5 minutes and nearly completely hardened in 15 minutes. Despite its low density, this foam is very rigid and serves as a good "pocket" for restraining the animal and reproducibly positioning the animal over a time series of scans.

Example 17

Protocol to Make a Multi-chamber Embryo Holder:

In this embodiment, an embryo holder is made up of the urethane foam (U.S. Composites, West Palm Beach, Fla.) which is a two part, "pour in place" liquid that when combined will expand into a rigid, closed cell polyurethane foam. The foam used in this embodiment has a density of 2 pounds per cubic foot when cured, which is the lightest of its kind. The densities of the foam refer to the weight of the foam when cured per cubic foot. Higher densities will result in heavier, stronger foam, but for our application the foam having a density of 2 pounds per cubic foot when cured was found to be best suited.

The two parts of the foam are first measured and mixed together in a plastic container. The liquids are mixed vigorously for 25 seconds and then transferred into the special plastic mold. The plastic mold is also covered with a commercial available mold release wax (U.S. Composites, West Palm Beach, Fla.), that helps for easy release of the foam and avoids any damage to the plastic mold. Within a 45 seconds period the foaming process begins and the foam will fully expand in 5 minutes and be fairly hard in 15 minutes.

An exemplary embryo holder includes 4 layers to be included in a cylinder of 40 mm in diameter and 40 mm in length and can hold up to 90 embryos at a time. A top and bottom layer may, for instance, contain 15 chambers each and intermediate layers may contain 30 chambers each with dimensions of 5×6×8 mm, with total of 90 chambers. Other configurations including more or fewer chambers and/or layers having the same or different dimensions may be used.

Any patents or publications mentioned in this specification are incorporated herein by reference to the same extent as if each individual publication is specifically and individually indicated to be incorporated by reference.

The methods, devices, systems and compositions described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A process of producing a microCT image of a stained specimen, wherein said specimen is a whole non-human organism capable of fitting inside a microCT instrument, said process comprising:
   (a) incubating a specimen in a first staining composition, the first staining composition comprising a first staining agent, to produce a stained specimen;
   (b) suspending said stained specimen in a liquid with an electron density lower than that of said stained specimen; and
   (c) scanning the stained specimen in an X-ray computed tomography scanner to produce said microCT image of said stained specimen.

2. The process of claim 1 wherein the specimen is selected from the group consisting of an ex vivo embryo and an ex vivo fetus.

3. The process of claim 1, wherein said process further comprises screening the specimen for phenotype, wherein said screening comprises: comparing the micro-CT image of the stained specimen to a statistically-averaged, age-matched atlas of a control specimen to determine differences between the images, thereby screening the specimen for phenotype.

4. The process of claim 3 wherein the computed tomography image of the specimen comprises an isosurface or semi-transparent rendering of the specimen.

5. The process of claim 3 wherein the computed tomography image of the specimen comprises a virtual section of the specimen.

6. The process of claim 1 further comprising exposing the specimen to a second staining agent prior to step (c) to produce a double-stained specimen.

7. The process of claim 6 wherein the second staining agent is present in the first staining composition.

8. The process of claim 6 wherein the second staining agent is present in a second staining composition.

9. The process of claim 1 wherein the first staining agent comprises 0.1 to 1.84 weight percent osmium tetroxide or 4.5 to 5.5 weight percent phosphotungstic acid.

10. The process of claim 6 wherein the first or second staining composition comprises a cacodylate buffer.

11. The process of claim 6 wherein the first staining composition or second staining composition comprises an organic fixative.

12. The process of claim 11 wherein the organic fixative is selected from the group consisting of: glutaraldehyde, formaldehyde, and a combination thereof.

13. The process of claim 1 wherein the first staining agent is selected from the group consisting of: ethidium bromide, cis-platin, and a combination thereof.

14. The process of claim 1 wherein the first staining agent is a cell or organelle membrane marker.

15. The process of claim 1 wherein the first staining agent is a nuclear marker.

16. The process of claim 1 wherein the specimen comprises a reporter gene product and incubating the specimen in the first staining composition produces a stain indicative of the presence of the reporter gene product.

17. The process of claim 16 wherein the reporter gene product is a beta-galactosidase.

18. The process of claim 1 further comprising obtaining a second microCT image from the specimen.

19. The process of claim 18 wherein a therapeutic or investigate procedure is performed subsequent to obtaining the first microCT image and prior to obtaining the second microCT image.

20. The process of claim 1, wherein prior to step (c) the specimen is placed in a specimen holder, said holder comprising: multiple chambers, each chamber having a wall having a support portion for support of the specimen placed in the chamber; and a liner in contact with the specimen to prevent contact of the specimen with the wall, at least a portion of the liner in contact with the specimen being highly transparent to electromagnetic radiation used to produce the microCT image.

21. The process of claim 1, wherein prior to step (c), the specimen is placed in a specimen holder, said specimen holder comprising: a wall having a support portion; and a bed for the specimen, the bed disposed on the support portion of the wall, the bed having a top side having a specimen contact portion and a bottom side, and a thickness extending between the top side and the bottom side, the specimen contact portion of the top side of the bed and the portion of the thickness adjacent to the top side being highly transparent to electromagnetic radiation used in the scanning step (c).

22. The process of claim 21, wherein the wall defines an internal volume and an exterior, the wall having a passage for placing the specimen in the internal volume.

23. The process of claim 21, further comprising a lid contacting the wall for closing the passage.

24. The process of claim 21, further comprising a gas control system.

25. The process of claim 21, wherein at least a portion of the wall is substantially transparent to electromagnetic radiation used in the scanning step (c).

26. The process of claim 25 wherein the gas control system includes a component selected from the group consisting of: a closable port in the wall defining a passage for a gas, a gasket, a filter, a gas pump, an anesthesia delivery device and a combination thereof.

27. The process of claim 21, further comprising a fiducial or co-registration marker in contact with a component of the holder present in the imaging field when in place in an imaging device.

28. The process of claim 21, wherein the bed has a density within the range of 1.8 to 8 pounds per cubic foot.

29. The process of claim 1, further comprising:
repeating step (c) to generate a first imaging dataset and a second imaging dataset from the specimen, wherein the specimen is secured in the same position for both the first and second imaging datasets; and co-registering the first imaging dataset and the second imaging dataset to produce a combined imaging dataset.

30. The process of claim 1, wherein prior to step (c), the specimen is placed in a specimen holder for supporting the specimen and maintaining the specimen in a desired position during said scanning step (c), the specimen holder comprising: a wall having a support portion; and a bed disposed on the support portion of the wall, the bed adapted to conform to at least a part of the specimen.

* * * * *

UNITED STATES PATENT AND TRADEMARK OFFICE
CERTIFICATE OF CORRECTION

| | | |
|---|---|---|
| PATENT NO. | : 8,189,737 B2 | Page 1 of 1 |
| APPLICATION NO. | : 12/162376 | |
| DATED | : May 29, 2012 | |
| INVENTOR(S) | : Keller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 532 days.

Signed and Sealed this
Seventh Day of August, 2012

David J. Kappos
*Director of the United States Patent and Trademark Office*